United States Patent [19]
Jacobsen et al.

[11] Patent Number: 5,594,140
[45] Date of Patent: Jan. 14, 1997

[54] IMIDAZO[1,5-A]QUINOLINES FOR TREATMENT OF ANXIETY AND SLEEP DISORDERS

[75] Inventors: Eric J. Jacobsen, Plainwell; Ruth E. TenBrink, Richland, both of Mich.

[73] Assignee: The Upjohn Company, Kalamazoo, Mich.

[21] Appl. No.: 640,973

[22] PCT Filed: Oct. 27, 1994

[86] PCT No.: PCT/US94/12197

§ 371 Date: May 13, 1996

§ 102(e) Date: May 13, 1996

[87] PCT Pub. No.: WO95/14020

PCT Pub. Date: May 26, 1995

Related U.S. Application Data

[63] Continuation of Ser. No. 242,556, May 13, 1994, abandoned, which is a continuation-in-part of Ser. No. 155,405, Nov. 19, 1993, abandoned.

[51] Int. Cl.⁶ .................................................. C07D 471/04
[52] U.S. Cl. ............................ 544/126; 544/361; 546/84
[58] Field of Search ...................... 544/126, 361; 546/84

[56] References Cited

U.S. PATENT DOCUMENTS 3,668,208  6/1972  Baxter ........................................ 546/84

FOREIGN PATENT DOCUMENTS 283162  9/1988  European Pat. Off. .

*Primary Examiner*—Robert W. Ramsuer
*Attorney, Agent, or Firm*—Bruce Stein

[57] ABSTRACT

Imidazo[1,5-a]quinolines of formula (I) which are useful pharmaceutical agents for the treatment of anxiety, sleep disorders, panic states, convulsions and muscle disorders.

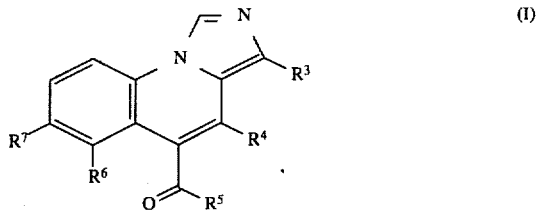

15 Claims, No Drawings

IMIDAZO[1,5-A]QUINOLINES FOR TREATMENT OF ANXIETY AND SLEEP DISORDERS

This application is a national phase of International Application No. PCT/US94/12197, International Filling Date 27 Oct. 1994, which is a continuation of U.S. patent application Ser. No. 08/242,556, filed May 13, 1994, now abandoned, which is a continuation-in-part of U.S. patent application Ser. No. 08/155,405, filed Nov. 19, 1993, now abandoned.

BACKGROUND OF THE INVENTION

1. Field of the Invention

The present invention is to imidazo[1,5-a]quinolines which are useful pharmaceutical agents for the treatment of anxiety, sleep disorders, panic states, convulsions and muscle disorders.

2. Description of the Related Art

EP 283,162 discloses imidazo[1,5-a]quinolines useful as anticonvulsants and anxiolytic agents, wherein only phenyl is attached to the $C_5$-position of the quinoline. These compounds lack a carbonyl group at the 5-position. The closest chemically structural compound in EP 283,162 to the present invention is 3-(3-cyclopropyl-1,2,4-oxadiazol-5-yl)-5-phenylimidazo[1,5a]quinoline which completely lacks affinity for the benzodiazepine receptor.

J. Her. Chem., 28, 1715 (1991) discloses imidazo[1,5-a]quinolines containing esters, acids, or amides at the 3-position. The 5-position is unsubstituted (5-H).

International Publication No. WO92/22552 discloses imidazo[1,5-a]quinoxalines which require a nitrogen atom at the 5-position for the treatment of anxiety and sleep disorders. The compounds of the present invention do not have nitrogen at the 5-position.

U.S. Pat. No. 4,838,925 discloses imidazo[1,5-a]quinoxalines which require a nitrogen atom at the 5-position and which are useful as agricultural chemicals. The compounds of the present invention do not have nitrogen at the 5-position.

Also known are the imidazo[1,2-a]quinolines. However, these compounds represent a different core structure of the 5-membered imidazo ring. Further, they do have a carbonyl at the 5-position. Because of their core structural differences they cannot have an ester, aryl, or oxadiazole groups attached at the 3-position as they contain an imidazole nitrogen at this site.

SUMMARY OF INVENTION

Disclosed are imidazo[1,5-a]quinolines of formula (I)

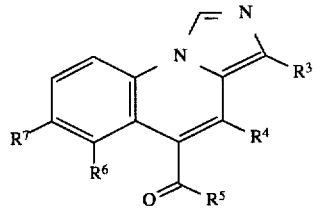

(I)

where (I) $R_3$ is
- (A) —CO—$OR_{3-1}$ where $R_{3-1}$ is
  - (1) —H,
  - (2) $C_1$–$C_6$ alkyl,
  - (3) $C_3$–$C_7$ cycloalkyl,
  - (4) —($C_1$–$C_6$ alkyl)—$C_3$–$C_7$ cycloalky,
  - (5) —$(CH_2)_n$—$CF_3$ where n is 0 thru 4,
  - (6) —$(CH_2)_n$—$CHF_2$ where n is defined above,
  - (7) —$(CH_2)_n$—$CH_2F$ where n is defined above,
  - (8) —φ optionally substituted with one or two
    - (a) —F,
    - (b) —Cl,
    - (c) —Br,
    - (d) —I,
    - (e) $C_1$–$C_4$ alkyl.
  - (f) —$NR_{3-2}R_{3-3}$ where $R_{3-2}$ and $R_{3-3}$ are the same or different and are selected from the group consisting of
    - (i) —H,
    - (ii) $C_1$–$C_6$ alkyl,
    - (iii) $C_3$–$C_7$ cycloalkyl,
    - (iv) —($C_1$–$C_4$ alkyl)—$C_3$–$C_7$ cycloalkyl, and where $R_{3-2}$ and $R_{3-3}$ are taken together with the attached nitrogen atom to form a heterocyclic moiety selected from the group consisting of pyrrolidinyl, morpholinyl, piperazinyl and piperidinyl,
- (B) —CO—$R_{3-5}$ where $R_{3-5}$ is
  - (1) —H,
  - (2) $C_1$–$C_6$ alkyl.
  - (3) —φ optionally substituted with one or two
    - (a) —F,
    - (b) —Cl,
    - (c) —Br,
    - (d) —I,
    - (e) $C_1$–$C_4$ alkyl,
    - (f) —$NR_{3-2}R_{3-3}$ where $R_{3-2}$ and $R_{3-3}$ are defined above,
- (C) aryl where aryl is
  - (1) phenyl

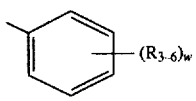

where w is 1 or 2 and where $R_{3-6}$ is
- (a) —H,
- (b) —F,
- (c) —Cl,
- (d) —Br,
- (e) —I,
- (f) —CN,
- (g) —$NO_2$,
- (h) —O—CO—$R_{3-1}$ where $R_{3-1}$ is defined above,
- (i) —$(CH_2)_n$—$CF_3$ where n is defined above,
- (j) $C_1$–$C_6$ alkyl,
- (k) $C_3$–$C_7$ cycloalkyl,
- (l) —($C_1$–$C_4$ alkyl)—$C_3$–$C_7$ cycloalkyl,
- (m) —$NR_{3-2}R_{3-3}$ where $R_{3-2}$ and $R_{3-3}$ are defined above,
- (n) —$(CH_2)_n$—O—$R_{3-1}$ where $R_{3-1}$ and n are defined above,
- (o) —$(CH_2)_n$—S—$R_{3-1}$ where $R_{3-1}$ and n are defined above,
- (p) —$(CH_2)_n$—CO—O—$R_{3-1}$ where $R_{3-1}$ and n are defined above,
- (q) —$NR_{3-1}$—CO—$R_{3-1}$ where the $R_{3-1}$'s are the same or different and are defined above,
- (r) —$SO_2$–$NR_{3-2}R_{3-3}$ where $R_{3-2}$ and $R_{3-3}$ are defined above,
- (s) —CO—$R_{3-5}$ where $R_{3-5}$ is defined above,
- (t) —NH—$SO_2$—$CH_3$, (u) —CO—N(R$_{3-4}$)$_2$ where the R$_{3-4}$ may be the same or different and are —H or C$_1$–C$_3$ alkyl,
(2) 5-substituted-1,2,4-oxadiazol-3-yl

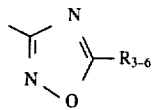

where R$_{3-6}$ is defined above,
(3) 3-substituted-1,2,4-oxadiazol-5-yl

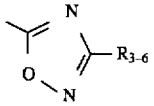

where R$_{3-6}$ is as defined above,
(4) 4- or 5-substituted isoxazol-3-yl

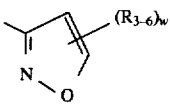

where w and R$_{3-6}$ are defined above,
(5) 3- or 4-substituted isoxazol-5-yl

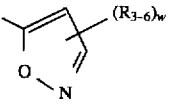

where w and R$_{3-6}$ are defined above;
(II) R$_4$ is
  (A) —H,
  (B) C$_1$–C$_4$ alkyl,
  (C) —CF$_3$;
(III) R$_5$ is
  (A) C$_1$–C$_6$ alkyl,
  (B) —φ optionally substituted with 1 or 2
    (1) —F,
    (2) —Cl,
    (3) —Br,
    (4) —I,
    (5) —CN,
    (6) —NO$_2$,
    (7) —O—CO—R$_{5-1}$ where R$_{5-1}$ is
      (a) —H,
      (b) C$_1$–C$_6$ alkyl,
      (c) C$_3$–C$_7$ cycloalkyl,
      (d) —(C$_1$–C$_6$ alkyl)—C$_3$–C$_7$ cycloalkyl,
      (e) —(CH$_2$)$_b$—CF$_3$ where b is 0 thru 4,
      (f) —(CH$_2$)$_b$—CHF$_2$ where b is defined above,
      (g) —(CH$_2$)$_b$—CH$_2$F where b is defined above,
    (8) —(CH$_2$)$_b$—CF$_3$ where b is defined above,
    (9) C$_1$–C$_6$ alkyl,
    (10) C$_3$–C$_7$ cycloalkyl,
    (11) —(C$_1$–C$_4$ alkyl)—C$_3$–C$_7$ cycloalky,
    (12) —NR$_{5-2}$R$_{5-3}$ where R$_{5-2}$ and R$_{5-3}$ are the same or different and are defined above,
    (13) —(CH$_2$)$_b$—O—R$_{5-1}$ where R$_{5-1}$ and b are defined above,
    (14) —(CH$_2$)$_b$—S—R$_{5-1}$ where R$_{5-1}$ and b are defined above,
    (15) —(CH$_2$)$_b$—CO—O—R$_{5-1}$ where R$_{5-1}$ and b are defined above,
    (16) —NR$_{5-1}$—CO—R$_{5-1}$ where the R$_{5-1}$'s are the same or different and are defined above,
    (16) —SO$_2$—NR$_{5-2}$R$_{5-3}$ where R$_{5-2}$ and R$_{5-3}$ are defined above,
    (18) —CO—R$_{5-4}$ where R$_{5-4}$ is
      (a) —H,
      (b) C$_1$–C$_6$ alkyl,
      (c) —N(R$_{5-1}$)$_2$ where the R$_{5-1}$s are the same or different and are as defined above,
(C) —O—R$_{5-5}$ where R$_{5-5}$ is
  (1) —H,
  (2) C$_1$–C$_6$ alkyl,
  (3) C$_3$–C$_7$ cycloalkyl,
  (4) —(C$_1$–C$_6$ alkyl)—C$_3$–C$_7$ cycloalkyl,
  (5) —(CH$_2$)$_b$—CF$_3$ where b is defined above,
  (6) —(CH$_2$)$_{CHF2}$ where b is defined above,
  (7) —(CH$_2$)$_b$—CH$_2$F where b is defined above,
  (8) —φ optionally substituted with one or two
    (a) —F,
    (b) —Cl,
    (c) —Br,
    (d) —I,
    (e) C$_1$–C$_4$ alkyl,
    (f) —NR$_{5-2}$R$_{5-3}$ where R$_{5-2}$ and R$_{5-3}$ are defined above,
(D) —NR$_{5-6}$R$_{5-7}$ where R$_{5-6}$ and R$_{5-7}$ are the same or different and are selected from the group consisting of
  (1) —H,
  (2) C$_1$–C$_6$ alkyl,
  (3) C$_3$–C$_7$ cycloalkyl,
  (4) —(C$_1$–C$_4$ alkyl)—C$_3$–C$_7$ cycloalky, and where R$_{5-6}$ and R$_{5-7}$ are taken together with the attached nitrogen atom to form a heterocyclic moiety selected from the group consisting of
  (a)

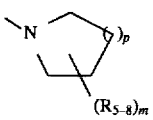

where m is 1 thru 4, p is 0 thru 4 and R$_{5-8}$ is selected from the group consisting of
  (i) —H,
  (ii) C$_1$–C$_6$ alkyl,
  (iii) C$_3$–C$_7$ cycloalkyl,
  (iv) —(C$_1$–C$_6$ alkyl)—C$_3$–C$_7$ cycloalkyl,
  (v) —(CH$_2$)$_b$—CF$_3$ where b is defined above,
  (vi) —(CH$_2$)$_{b-CHF2}$ where b is defined above,
  (vii) —(CH$_2$)$_b$—CH$_2$F where b is defined above,
  (viii) —φ optionally substituted with 1 or 2
  (I) —F,
  (II) —Cl,
  (III) —Br,
  (IV) —I,
  (V) C$_1$–C$_4$ alkyl,
  (VI) —NH$_2$,
  (VII) —CO—NH$_2$,
  (VIII) —SO$_2$—NH$_2$,
  (IX) —NH—SO$_2$—CH$_3$, (b)

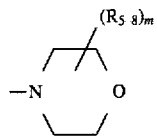

where m and $R_{5-8}$ are defined above,
(c)

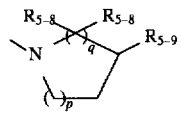

where q is 1 or 2, where p and $R_{5-8}$ are defined above and where $R_{5-9}$ is
(A) —H,
(B) $C_1$–$C_6$ alkyl,
(C) $C_3$–$C_7$ cycloalkyl,
(D) —($C_1$–$C_6$ alkyl)—$C_3$–$C_7$ cycloalkyl,
(E) —$(CH_2)_b$—$CF_3$ where b is defined above,
(F) —$(CH_2)_b$—$CHF_2$ where b is defined above,
(G) —$(CH_2)_b$—$CH_2F$ where b is defined above,
(H) —φ optionally substituted with one or two
(1) —F,
(2) —Cl,
(3) —Br,
(4) —I,
(5) $C_1$–$C_4$ alkyl,
(6) —$NH_2$,
(d)

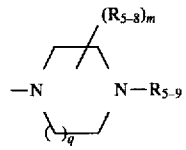

where m, q, $R_{5-8}$ and $R_{5-9}$ are defined above,
(e)

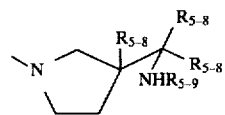

where $R_{5-8}$ and $R_{5-9}$ are defined above,
(f)

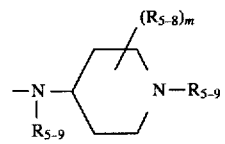

where m, $R_{5-8}$ and $R_{5-9}$ are defined above,
(IV) $R_6$ is
(A) —H,
(B) —F,
(C) —Br,
(D) —I,
(E) $C_1$–$C_4$ alkyl,
(F) —CN,
(G) —$NO_2$,
(H) —$(CH_2)_g$—$CF_3$ where g is 0 thru 4, (I) —$(CH_2)_g$—$OR_{6-1}$ where $R_{6-1}$ is
(1) —H,
(2) $C_1$–$C_6$ alkyl,
(3) —φ optionally substituted with one or two
(a) —F,
(b) —Cl,
(c) —Br,
(d) —I,
(e) $C_1$–$C_4$ alkyl,
(f) —$NR_{6-2}R_{6-3}$ where $R_{6-2}$ and $R_{6-3}$ are the same or different and are selected from the group consisting of
(i) —H,
(ii) $C_1$–$C_6$ alkyl,
(iii) $C_3$–$C_7$ cycloalkyl,
(iv) —($C_1$–$C_4$ alkyl)—$C_3$–$C_7$ cycloalkyl, and where $R_{6-2}$ and $R_{6-3}$ are taken together with the attached nitrogen atom to form a heterocyclic moiety selected from the group consisting of pyrrolidinyl morpholinyl, piperazinyl, piperdinyl,
(J) —CO—O—$R_{6-4}$ where $R_{6-4}$ is
(1) —H,
(2) $C_1$–$C_6$ alkyl,
(3) $C_3$–$C_7$ cycloalkyl,
(4) —($C_1$–$C_6$ alkyl)—$C_3$–$C_7$ cycloalkyl,
(5) —$(CH_2)_g$—$CF_3$ where g is defined above,
(6) —$(CH_2)_g$—$CHF_2$ where g is defined above,
(7) —$(CH_2)_g$—$CH_2F$ where g is defined above,
(8) —φ optionally substituted with one or two
(a) —F,
(b) —Cl,
(c) —Br,
(d) —I,
(e) $C_1$–$C_4$ alkyl,
(f) —$NR_{6-2}R_{6-3}$ where $R_{6-2}$ and $R_{6-3}$ are as defined above,
(K) —CO—$NR_{6-2}R_{6-3}$ where $R_{6-2}$ and $R_{6-3}$ are as defined above,
(L) —$(CH_2)_g$—$NR_{6-2}R_{6-3}$ where g, $R_{6-2}$ and $R_{6-3}$ are defined above,
(M) —NH—CO—$R_{6-4}$ where $R_{6-4}$ is defined above,
(N) —$SO_2$—$NR_{6-2}R_{6-3}$ where $R_{6-2}$ and $R_{6-3}$ are defined above,
(O) —$N_3$;
(V) $R_7$ is
(A) —H,
(B) —F,
(C) —Br,
(D) —I,
(E) $C_1$–$C_4$ alkyl,
(F) —CN,
(G) —$NO_2$,
(H) —$(CH_2)_g$—$CF_3$ where g is 0 thru 4,
(I) —$(CH_2)_g$—$OR_{7-1}$ where $R_{7-1}$ is
(1) —H,
(2) $C_1$–$C_6$ alkyl,
(3) —φ optionally substituted with one or two
(a) —F,
(b) —Cl,
(c) —Br,
(d) —I,
(e) $C_1$–$C_4$ alkyl,
(f) —$NR_{7-2}R_{7-3}$ where $R_{7-2}$ and $R_{7-3}$ are the same or different and are selected from the group consisting of
(i) —H, (ii) $C_1$–$C_6$ alkyl,
(iii) $C_3$–$C_7$ cycloalkyl,
(iv) —($C_1$–$C_4$ alkyl)—$C_3$–$C_7$ cycloalkyl, and where $R_{6-2}$ and $R_{7-3}$ are taken together with the attached nitrogen atom to form a heterocyclic moiety select from the group consisting of pyrrolidinyl, morpholinyl, piperazinyl, piperdinyl, (J) —CO—O—$R_{7-4}$ where $R_{7-4}$ is
  (1) —H,
  (2) $C_3C_6$ alkyl,
  (3) $C_3$–$C_7$ cycloalkyl,
  (4) —($C_1$–$C_6$ alkyl)—$C_3$–$C_7$ cycloalkyl,
  (5) —$(CH_2)_g$—$CF_3$ where g is defined above,
  (6) —$(CH_2)_g$—$CHF_2$ where g is defined above,
  (7) —$(CH_2)_g$—$CH_2$ F where g is defined above,
  (8) —φ optionally substituted with one or two
    (a) —F,
    (b) —Cl,
    (c) —Br,
    (d) —I,
    (e) $C_1$–$C_4$ alkyl,
    (f) —$NR_{7-2}R_{7-3}$ where $R_{7-2}$ and $R_{7-3}$ are as defined above, (K) —CO—$NR_{7-2}R_{7-3}$ where $R_{7-2}$ and $R_{7-3}$ are as defined above,
(L) —$(CH_2)_g$—$_{NR7-2}R_{7-3}$ where g, $R_{7-2}$ and $R_{7-3}$ are defined above,
(M) —NH—CO—$R_{7-4}$ where $R_{7-4}$ is defined above,
(N) —$SO_2$—$NR_{7-2}R_{7-3}$ where $R_{7-2}$ and $R_{7-3}$ are defined above,
(O) —$N_3$; and pharmaceutically acceptable salts thereof which are useful for the treatment of anxiety, sleep disorders, panic states, convulsions and muscle disorders.

DETAILED DESCRIPTION OF THE INVENTION

The imidazo[1,5-a]quinolines (I) are produced by a number of processes depending on the variable substituents involved, particularly those at positions 3, 4, 5, 6, and 7. In all cases the process to produce the imidazo[1,5-a]quinolines (I) can be viewed as a two step process, as will be explained in more detail below. The first part is the transformation of the appropriately substituted isatin compound to bicyclic amide or ketone (VI or X). The second part is the addition of the appropriately substituted imidazo group by condensation with an isocyanide reagent (IX). Because imidazo[1,5-a]quinolines (I) are novel, the overall chemical process is novel. However it is realized that each step is known to those skilled in the art. The combination of known process chemistry in a novel way produces the novel imidazo[1,5-a]quinolines.

CHART B discloses one of the general processes for the transformation of isatin (III) to amide or ketone (VI) and the subsequent conversion of this compound to imidazo[1,5-a]quinoline (I). The substituted isatin precursors (III) are either commercially available or are known to those skilled in the art. Following the general procedure of Camp (Arch. Pharm. 237, 687 (1899)) the appropriately substituted isatin ((III) was acylated with either acetic anhydride or propionic anhydride to provide isatin amide (IV). Generally these reactions were carried out in a solvent such as THF in the presence of dimethylaminopyridine, between 20°–25° and that of the solvent system at reflux. Reaction of isatin amide (IV) with 1N sodium hydroxide or 1N potassium hydroxide at reflux, in the presence or absence of THF, provides the appropriately substituted 2-hydroxyquinoline-4-carboxylic acid (V). Alternatively, the substituted 2-hydroxyquinoline-4-carboxylic acid (V) may be formed directly from isatin (III) by reaction of isatin (III) with malonic acid in THF at reflux and then removal of the solvent under reduced pressure, heating the crude material in water at reflux. This is the preferred method when $R_4$ and $R_6$ are hydrogen and $R_7$ is —Cl. Reaction of the acid (V) with thionyl chloride at reflux provides an intermediate acid chloride (V-A) upon concentration. Exposure of this crude acid halide (V-A) to the desired amine in an inert solvent such as methylene chloride or THF in the presence of an acid scavenger such as Hunig's base or triethylamine between 0°→25° gives the desired amide intermediate (VI).

The formation of the desired imidazo[1,5-a]quinoline (I) from the amide (VI) could be accomplished by one of two methods. Treatment of the amide (VI) with potassium tert-butoxide followed by diethyl chlorophosphate in a solvent such as THF or DMF at low temperatures (between −78° and 0°), provides an intermediate phosphonate imine (VII) which typically without isolation was reacted with the appropriate isocyanide reagent (IX) in the presence of an additional equivalent of potassium tert-butoxide [from −78° to room temperature (20°–25°)], to give imidazo[1,5-a] quinoline (I). This general imidazole ring forming procedure is known, see J. Med. Chem., 32, 2282 (1989). An alternative procedure to provide imidazo[1,5-a]quinoline (I) was to react the amide (VI) with trifluoromethanesulfonic anhydride in an inert solvent such as dichloromethane in the presence of a base such as pyridine. The intermediate triflate (VIII) could be isolated and even purified by conventional means such as flash chromatography. Reaction of the triflate (VIII) with the isocyanide reagent (IX) in THF or DMF in the presence of potassium tert-butoxide gives the imidazo [1,5-a]quinoline (I). Both processes work well when $R_3$ is aromatic, however when $R_3$ is an ester substituent, then reaction via the triflate intermediate (VIII) is the best procedure.

CHART C provides an alternative sequence useful for the preparation of the imidazo[1,5-a]quinoline (I). Reaction of the acid (V) with thionyl chloride at reflux in the presence of a catalytic amount of DMF provides the dichloride intermediate (VB) upon cooling and concentration. This intermediate (VB) was generally carried on without further purification. Reaction of the crude dichloride intermediate (XB) with an amine in the presence of an acid scavenger such as Hunig's base in methylene chloride at 0°→25° as described for CHART B provides the desired amide (X). Reaction of this amide (X) with the isocyanide reagent (IX) in the presence of potassium tert-butoxide in THF or DMF as described for CHART B provides the desired imidazo[1,5-a]quinoline (I). This is the preferred process when the $R_5$ group contains a reactive hydrogen (OH, NH, SH). This process also works well when $R_3$ is an ester substituent.

In some cases a protecting group may be attached to the $R_5$ substituent. As shown in CHART D the protected piperazine (XII n=1) is prepared by reaction of acid (V) with thionyl chloride and DMF, followed by treatment with protected piperazine (XI) in a similar fashion to that reported for CHART C, to give (XI-A) and finally cyclization with isocyanide (IX) to give (XII). Suitable protecting groups include CBZ and t-BOC derivatives. Deprotection following conventional methods suitable for the desired protecting group known to those skilled in the art gives the imidazo [1,5-a]quinoline (I). This sequence is also applicable for other $R_5$ groups (ketones, esters) which also contain a protecting group.

CHART E discloses an alternative sequence for the preparation of imidazo[1,5-a]quinolines (I) which contain a polymethylated piperazine for $R_5$. Following the general procedure as described above in CHART C, acid (V) upon reaction with thionyl chloride and DMF followed by exposure to the protected amine (XIV) in methylene chloride in the presence of Hunig's base at 0°→25° provides carbamate (XIII). Suitable protecting groups include CBZ and t-BOC derivatives. Deprotection of carbamate (XIII) by treatment with trifluoroacetic acid (for t-BOC) in a solvent such as methylene chloride at 0° gives amino alcohol (XV). Amino alcohol (XV) was cyclized by treatment with diethyl azodicarboxylate (DEAD) in THF in the presence of triphenylphosphine to provide amide (X) where $R_5$ is a polymethylated piperazine. This latter procedure is especially useful for the synthesis of trans-3,5-dimethylpiperazine amide analogs in racemic or enantiomeric form. Amide (X) is converted to imidazo[1,5-a]quinoline (I) as described previously for CHARTs B and C.

CHART F discloses how to prepare the requisite amine (XIV) used in CHART E. Reaction of t-BOC-alanine (XVI, R or S) with 1,1'-carbonyldiimidazole (CDI) as a condensing agent in an inert solvent such as THF or methylene chloride followed by treatment with amino alcohol (XVII, racemate, or R or S enantiomer) at 20°–25° gives amide (XVIII). Reduction of amide (XVIII) using a reducing agent such as borane dimethyl sulfide complex in THF at 20°–25° followed by addition of aqueous potassium hydroxide and heating at reflux provides amine (XIV), which was utilized as described in CHART E.

CHART G discloses the preparation of protected 2-methylpiperazines (XXIII) in enantiomeric form. While 2-methylpiperazine has been resolved (J. Med. Chem. 33, 1645, (1990)), it was found advantageous to prepare the compound in protected form (to facilitate coupling) directly from enantiopure materials. Activation of t-BOC-alanine (XVI, R or S) with CDI in THF or methylene chloride followed by N-benzylethanolamine at 20°–25° provides amide (IXX). Deprotection of the t-butyl carbamate group of this amide (IXX) with trifluoroacetic acid in methylene chloride at 0° followed by cyclization of the intermediate amino alcohol using DEAD and triphenylphosphine in THF at 20°–25° as described above for CHART E provides piperazine-2-one (XX). Reduction of the piperazine-2-one intermediate (XX) with lithium aluminum hydride in THF between 20°–25° and 80° provides 1-benzyl-3-methylpiperazine (XXI). BOC-protection of this piperazine (XXI) by reaction with di-tert-butyl dicarbonate in THF or methylene chloride at 20°–25° provides bis-protected piperazine (XXII). Hydrogenation of bis-protected piperazine (XXII) using Pearlman's catalyst in ethanol at 20°–25° gives the desired protected 2-methylpiperazine (XXIII) in enantiomeric form.

Imidazo[1,5-a]quinolines which are ketones or esters at $R_5$ are prepared most conveniently as disclosed in CHART H. Reaction of acid (V) with thionyl chloride and DMF at reflux, followed by hydrolysis of the intermediate acid halide with aqueous sodium hydroxide provides acid (XXIV). Cyclization of acid (XXIV) with the isocyanide reagent (IX) in the presence of at least 2.0 eq of potassium tert-butoxide in DMF as described above for CHART B gives the imidazo[1,5-a]quinoline acid (XXV). Reformation of the acid halide of imidazo[1,5-a]quinoline acid (XXV) was accomplished with thionyl chloride as described above, which was subsequently reacted with either an amine or alkoxide in THF or methylene chloride in the presence of a suitable base if necessary. Alternatively, the crude acid chloride could be reacted with an alkyl or aryl cuprate, organolithium, or Grignard reagent to provide imidazo[1,5-a]quinoline (I) where $R^5$ is an alkyl or aryl group. One may also react the acid halide with a Lewis acid such as aluminum trichloride in benzene or an appropriately substituted aromatic compound to provide imidazo[1,5-a]quinoline (I).

Chart I discloses the preparation of both enantiomers of 2,6,6-trimethylpiperazine (XXXI). Protection of 1,1-dimethylethylenediamine (XXVI) with trityl chloride in a solvent such as dichloromethane in the presence of an acid scavenger such as triethylamine provides protected diamine (XXVII). Alkylation of the protected diamine (XXVII) with the triflate of the desired enantiomer of methyl lactate (XXVIII) in a solvent such as dichloromethane gives the ester (XXIX). Cyclization of ester (XXIX) in acetic acid at 25°–100° provides the lactam (XXX). Reduction of the lactam (XXX) with lithium aluminum hydride in THF at 20°–25° gives the trimethylpiperazine (XXXI) which is isolated most conveniently as the (dihydrochloride) salt.

The imidazo[1,5-a]quinoxalines (I) are amines. Many do not form salts, some do. If salts can be made it is preferable to make them because of their increased water solubility. When salts of the imidazo[1,5-a]quinoxalines (I) are made they are produced by reaction with acids of sufficient strength. Pharmaceutically acceptable salts include salts of both inorganic and organic acids. The preferred pharmaceutically acceptable salts include salts of the following acid methanesulfonic, hydrochloric, hydrobromic, sulfuric, phosphoric, nitric, benzoic, citric, tartaric, fumaric, maleic, $CH_3-(CH_2)_n-COOH$ where n is 0 thru 4, $HOOC-(CH_2)_n-COOH$ where n is as defined above.

The imidazo[1,5-a]quinoxalines (I) of the present invention have relatively more anxiolytic and less sedative activity than other known anxiolytic compounds such as diazepam and therefore are useful as anxiolytic agents at lower doses and as sedatives at higher doses.

The imidazo[1,5-a]quinoxalines (I)) are active orally or parenterally. Orally the imidazo[1,5-a]quinoxalines (I) can be given in solid dosage forms as tablets or capsules, or can be given in liquid dosage forms such as elixirs, syrups or suspensions as is known to those skilled in the art. It is preferred that the imidazo[1,5-a]quinoxalines (I) be given in solid dosage form and that it be a tablet.

For anxiolytic effect the imidazo[1,5-a]quinoxalines (I) should be give in amount of about 0.125 mg to about 100 mg/person, one to three times a day. Preferably, about 0.25 to about 50 mg/day in divided doses.

For sedative/hypnotic effect the imidazo[1,5-a]quinoxalines (I) should be given in the amount of about 0.125 mg to about 500 mg/person, preferably at bedtime or when sedation is needed. It is preferred the sedative/hypnotic dose be from about 0.25 mg to about 50 mg/person.

The exact dosage and frequency of administration depends on the particular imidazo[1,5-a]quinoxalines (I) used, the particular condition being treated, the severity of the condition being treated, the age, weight, general physical condition of the particular patient, other medication the individual may be taking as is well known to those skilled in the art and can be more accurately determined by measuring the blood level or concentration of the imidazo[1,5-a]quinoxalines (I) in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)H$. Groups $R_i$ and $R_j$ would represent monovalent variable substituents if attached to the formula $CH_3$—$CH_2$—$C(R_i)(R_j)$—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$—the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom. i.e., by the symbol "- - -" or "...". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —$C(α-R_{i-j})(β-R_{i-k})$—. For example, when the bivalent variable $R_6$, —$C(=R_6)$— is defined to consist of two monovalent variable substituents, the two monovalent variable substituents are α-$R_{6-1}$:β-$R_{6-2}$, ... α-$R_{6-9}$:-$R_{6-10}$, etc, giving —$C(α-R_{6-1})(β_{6-2})$—, ... —$C(α-R_{6-9})(α-R_{6-10})$—,etc. Likewise, for the bivalent variable $R_{11}$, —$C(=R_{11})$—, two monovalent variable substituents are α-$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group -X-Y-, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO— ..." means a lactone in which the carbonyl is bonded to $C_2$. However, when designated "... $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.
THF refers to tetrahydrofuran.
BOC refers to t-butyl carbamate, $(CH_3)_3C$—O—CO—.
DMF refers to dimethylformamide.
Pearlman's catalyst refers to palladium hydroxide on carbon.
Hunig's base refers to diisopropylethylamine, $(CH_3)_2CH$—N—$CH_2CH_3$.
Chromatography (column and flash chromatography) refers purification/separation of compounds expressed as (support; eluent). It is understood that the appropriate fractions are pooled and concentrated to give the desired compound(s).
DMAP refers to dimethylaminopyridine, $(CH_3)_2N$-pyridin-1-yl.
TFA refers to trifluoracetic acid, $CF_3$—COOH.
CDI refers to 1,1'-carbonyldiimidazole.
Saline refers to an aqueous saturated sodium chloride mixture.
IR refers to infrared spectroscopy.
NMR refers to nuclear (proton) magnetic resonance spectroscopy, chemical shifts are reported in ppm ($\delta$) downfield from tetramethylsilane. —$\phi$ refers to phenyl ($C_6H_5$). $[\alpha]_D^{25}$ refers to the angle of rotation of plant polarized light (specific optical rotation) at 25° with the sodium D line (589A).
MS refers to mass spectrometry expressed as m/e or mass/charge unit. $[M+H]^+$ refers to the positive ion of a parent plus a hydrogen atom. EI refers to electron impact. CI refers to chemical ionization. FAB refers to fast atom bombardment.
Ether refers to diethyl ether.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).
When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1 1-[(2S)-[N-[(1,1-dimethylethoxy)carbonyl]]propylamino]amino-(2R)-propanol (XIV)

Step I. 1-[N-[(1,1-dimethylethoxy)carbonyl]-L-alanyl]amino-(2R)-propanol 1,1'-Carbonyldiimidazole (CDI, 3.44 g) is added to a mixture of BOC-(L)-alanine (XVI, 4.00 g) and methylene chloride (64 ml). The mixture is stirred for 1 hr at 20°–25°. (R)-1-Amino-2-propanol (XVII, 2.5 ml) is then added. The mixture is stirred for 16 hr at 20°–25° and is concentrated. Purification by flash chromatography (silica gel; ethyl acetate) gives the amide (XVIII) as an oil, IR (neat) 3308, 2978, 1694, 1659, 1530, 1368, 1250, 1170 $cm^{-1}$; NMR ($CDCl_3$) 6.45–6.6, 4.85–5.0, 4.13, 3.9–4.0, 3.35–3.5, 3.05–3.2, 1.45, 1.38, 1.19 $\delta$; MS (EI) 202, 173, 144, 102, 88.

Step II. 1-[(2S)-[N-[(1,1-dimethylethoxy)carbonyl]]propylamino]amino-(2R)-propanol (XIV)

Borane methyl sulfide complex (4.70 ml, 10.0M) is added to a mixture of the amide (XVIII, 4.54 g) and THF (110 ml). The mixture is stirred for 16 hr at 20°–25° and is quenched slowly with hydrochloric acid (10%). Water (40 ml) and potassium hydroxide (10.0 g) are added and the mixture heated at reflux for 26 hr. After cooling to 20°–25°, the organics are removed under reduced pressure. The aqueous layer is saturated with sodium chloride which is extracted several times with methylene chloride. The organic phase is dried (magnesium sulfate), filtered, and concentrated to give the title compound sufficiently pure to be carried on crude. A small portion is recrystallized from hot ether/hexane to give a solid, mp 77°–78°; $[\alpha]_D^{25}$-28° ($CHCl_3$); IR (mineral oil) 3374, 1683, 1525, 1177, 1160, 1093 $cm^{-1}$; NMR ($CDCl_3$) 4.45–4.65, 3.65–3.9, 2.5–2.85, 2.40, 2.05–2.5, 1.45, 1.15, 1.14 $\delta$; MS (EI) 214, 187, 159, 141, 131, 115 and 88.

PREPARATION 2 1-[(2R)-[N-[(1,1-dimethylethoxy)carbonyl]]propylamino]amino-(2S)-propanol (XIV)

The R,S-enantiomer is prepared in a similar fashion with identical spectral data (mp 72°–74°); $[\alpha]_D^{25}$ +28° ($CHCl_3$).

PREPARATION 3 tert-Butyl (2R)-methyl-1-piperazinecarboxylate (XXIII)

Step I. 1-N-benzyl-1-IN-[(1,1-dimethylethoxy)carbonyl]-D-alanyl]amino-2-ethanol (IXX)

CDI (6.88 g) is added to a mixture of BOC-(D)-alanine (XVI, 8.00 g) and THF (128 ml). The mixture is stirred for 1 hr at 20°–25°. A mixture of N-benzylethanolamine (6.66 g) and THF (20 ml) is then added. The mixture is stirred for 16 hr at 20°–25° and is concentrated. Purification by flash chromatography (silica gel; ethyl acetate/hexane (1.5/1)) gives the amide (IXX), IR (neat) 1705, 1638, 1452, 1367 and 1168 $cm^{-1}$NMR ($CDCl_3$) 7.15–7.45, 5.2–5.4, 5.01, 4.6–4.9, 4.33, 3.55–3.85, 3.25–3.55, 1.44, 1.43, 1.35 and 1.2–1.3 $\delta$; MS (EI) 322, 292, 266, 249, 178, 150 and 120.

Step II. 1-Benzyl-(3R)-methylpiperazine-2-one (XX)

Trifluoroacetic acid (50 ml) is added to a mixture of the amide (IXX, 11.1 g) and methylene chloride (100 ml) at 0°. The mixture is stirred at 0° for 1.75 hr and is concentrated. Partitioning of the residue between methylene chloride (4×60 ml) and sodium hydroxide (25%), drying of the combined organic layers over magnesium sulfate, and concentration provides the deprotected amine which is carried on crude, NMR ($CDCl_3$) 7.15–7.4, 4.68, 4.65, 3.95–4.1, 3.45–3.9, 3.15–3.3, 2.8–2.9, 2.35, 1.37 and 1.28 $\delta$. Diethyl azodicarboxylate (DEAD, 17.0 ml) is added to a mixture of the crude amine, triphenylphosphine (12.1 g) and THF (200 ml). The mixture is stirred at 20°–25° for 16 hr and is concentrated. Purification by flash chromatography (silica gel; ethyl acetate/methanol (4/1)), gives 1-benzyl-(3R)-methylpiperazine2-one (XX), IR (neat) 1637, 1496, 1453 and 702 cm$^{-1}$; NMR (CDCl$_3$) 7.2–7.4, 4.60, 3.62, 3.3–3.45, 3.1–3.25, 2.95–3.1, 1.66 and 1.45 δ; MS (EI) 204, 161, 113 and 91.

Step III. 1-Benzyl-(3R)-methylpiperazine (XXI)

A mixture of 1-benzyl-3R-methylpiperazine-2-one (XX, 4.36 g), lithium aluminum hydride (LAH, 2.33 g) and THF (125 ml) is heated at reflux for 16 hr. After cooling to 20°–25°, the mixture is quenched slowly with water (2.3 ml), sodium hydroxide (10%, 3.5 ml) and water (5.7 ml). The residue is diluted with ether (100 ml) and is stirred for 1 hr. The solids are filtered and washed successively with ether, methylene chloride and ether. The combined filtrates are dried over potassium carbonate, filtered and concentrated to give 1-benzyl-(3R)-methylpiperazine (XXI), sufficiently pure to be carried on crude, NMR (CDCl$_3$) 7.2–7.4, 3.49, 2.7–3.0, 1.95–2.1, 166, 1.3–1.7 and 1.01 δ.

Step IV. tert-Butyl 4-benzyl-(2R)-methyl-1-piperazinecarboxylate (XXII)

A mixture of di-tert-butyl dicarbonate (4.60 g) and methylene chloride (16 ml) is added dropwise over 10 min to a mixture of 1-benzyl-(3R)-methylpiperazine (XXI, 3.56 g) and methylene chloride (55 ml). After stirring for 16 hr at 20°–25°, the residue is partitioned between methylene chloride (3×40 ml) and sodium bicarbonate, the combined organic layers are dried over magnesium sulfate, filtered, concentrated, and purified by flash chromatography (silica gel; hexane/ethyl acetate, (3/1)) to give tert-butyl 4-benzyl-(2R)-methyl-1-piperazinecarboxylate (XXII); [α]$_D$ +45° (ethanol); IR (neat) 1695, 1411, 1365, 1177 and 1161 cm$^{-1}$; NMR (CDCl$_3$) 7.2–7.4, 4.1–4.25, 3.80, 3.47, 3.05–3.2, 2.77, 2.59, 2.12, 1.95–2.1, 1.45 and 1.24 δ; MS (EI) 290, 233, 160, 146 and 134.

Step V. tert-Butyl (2R)-methyl-1-piperazinecarboxylate (XXIII)

A mixture of tert-butyl 4-benzyl-(2R)-methyl-1-piperazinecarboxylate (XXII, 5.40 g), ethanol (200 ml) and Pearlman's catalyst (1.36 g) is hydrogenated (36 psi) for 16 hr at 20°–25° in a Parr flask. The mixture is filtered and the solids washed successively with ethanol, methylene chloride and methanol. The combined filtrates are concentrated, diluted with methylene chloride, filtered, and concentrated to give the title compound which solidified upon standing, mp 33°–36°; [α]$^{25}_D$ –59° (CHCl$_3$); IR (mineral oil) 1695, 1408, 1363, 1301, 1226, 1173 and 1095 cm$^{-1}$; NMR (CDCl$_3$) 4.1–4.3, 3.7–3.85, 2.6–3.05, 1.84, 1.46 and 1.22 δMS (EI) 200, 144, 127, 99, 70 and 57.

PREPARATION 4 tert-Butyl (2S)-methyl-1-piperazinecarboxylate (XXIII)

The (S)-enantiomer is prepared in an identical fashion with identical spectral data; [α]$^{25}_D$ +67°(CHCl$_3$).

PREPARATION 5 2,2,6(R)-Trimethylpiperazine (XXXI)

Step I. 1-N-(Triphenylmethyl)-1,2-diamino-2-methylpropane (XXVII) 27622-JWM-15

A mixture of 1.2-diamino-2-methylpropane (XXVI, 10 ml) and triethylamine (20 ml) in methylene chloride (400 ml) is cooled to –40°. Trityl chloride (26 g) in methylene chloride (75 ml) is added dropwise and the reaction is allowed to warm to 20°–25° and stir for 40 h. After a standard basic workup (methylene chloride, sodium bicarbonate and magnesium sulfate) the residue is chromatographed (silica gel; ethyl acetate/methanol, 9/1), to provide the desired compound, mp 97°–98°; IR (mineral oil) 2956, 2925, 2869, 2855, 1487, 1462, 1449, 747 and 708 cm$^{-1}$;NMR (CDCl$_3$) 7.51, 7.27, 7.17, 1.94–2.01, 1.71–1.82 and 1.12 δ; MS (m/e) 273, 258, 243, 165 and 58.

Step II. Methyl N-[2-methyl-3-(triphenylmethylamine)-2-propyl]-(R)-alanine (XXIX)

A mixture of methyl-(S)-(–)-lactate (XXVIII, 2.53 ml) in methylene chloride (130 ml) is cooled to 0°. Triflic anhydride (4.9 ml) is added and the reaction is stirred for 10 minutes at which time 2,6-lutidine (3.55 ml) is added. After an additional ten minutes of stirring at 0°, a mixture of 1-N-(triphenylmethyl)-1,2-diamino-2-methylpropane (XXVII, Step I, 7 g) and triethylamine (4.2 ml) in methylene chloride (50 ml) is added. The reaction is allowed to stir for 1 hr at 0° and 4 hr at 20°–25°. After a standard basic workup (methylene chloride, sodium bicarbonate, saline and magnesium sulfate) the residue is chromatographed (silica gel; hexane/ethyl acetate, 4/1), to provide the desired compound, mp 78°–80°; IR (mineral oil) 2954, 2924, 2853, 1734, 1457, 1451, 1197 and 709 cm$^{-1}$;NMR (CDCl$_3$) 7.50, 7.24–7.29, 7.17, 3.60, 1.71–2.93, 1.92–2.05, 1.13, 1.08 and, 1.00 δ; MS (m/e) 243, 165, 144 and 84.

Step III. 3(R),5,5-Trimethylpiperazin-2-one (XXX)

A mixture of methyl N-[2-methyl-3-(triphenylmethylamine)-2-propyl]-(R)-alanine (XXIX, Step II, 4.32 g) and acetic acid (15 ml) is stirred for 1 hr. Water (15 ml) is added and the reaction is heated at 100° for 2 hr. After cooling to 20°–25°, an additional water (10 ml) is added and the precipitated triphenylcarbinol is filtered off. Removal of the acetic acid and water from the filtrate under reduced pressure gives the desired compound as a solid, mp 145°–150°; IR (mineral oil) 2974, 2962, 2926, 1670, 1649, 1492, 1340, 1060 and 864 cm$^{-1}$NMR (CDCl$_3$) 6.45, 3.60, 3.26, 3.08, 1.38, 1.30 and 1.19; MS (m/e) 142, 127, 99, 84, 70 and 58.

Step IV. 2,2,6(R)-Trimethylpiperazine dihydrochloride (XXXI)

3(R),5,5-Trimethylpiperazin-2-one (XXX, Step III, 0.91 g) is added portionwise to a mixture of lithium aluminum hydride (0.45 g) in THF (40 ml). The reaction is allowed to stir at 20°–25° for 1 hr and at reflux for an additional 2 hr. After cooling to 20°–25° the reaction is quenched by the successive addition of water (0.5 ml), sodium hydroxide (15%, 0.5 ml) and water (1.5 ml). After stirring for 0.5 hr the solids are filtered off and the filtrate is dried over magnesium sulfate. The mixture is filtered and methanolic hydrochloric acid (5 ml) is added. After stirring for 1 hr the methanol is removed under reduced pressure and the remaining solid is triturated with ether to provide the title compound, mp >250°; IR (mineral oil) 2994, 2986, 2978, 2923, 1580, 1390 and 990 cm$^{-1}$; NMR (CD$_3$OD) 3.80–3.93.3.52–3.65, 3.15–3.30, 1.59, 1.56 and 1.45δ; MS (m/e) 128, 113 and 84; [α]$^{25}_{D1}$ –9° (methanol).

PREPARATION 6 2,2,6(S)-Trimethylpiperazine (XXXI)

Following the general procedure of PREPARATION 5 and making non-critical variations but starting with methyl-(R)-(–)-lactate (XXVIII), the title compound (the S-enantiomer of PREPARATION 5), is obtained (with identical spectral data); [α]$^{25}_D$ +9° (methanol).

Example 1

Pyrrolidino 3-(5-cyclopropyl-1,2,4-oxadiazol-3-yl)imidazo[1,5-a]quinoline-5-carboxamide (I)

Step I. Methyl 2-hydroxyquinoline-4-carboxylate (VI)

To 2-hydroxyquinoline-4-carboxylic acid (V. 5.52 g) is added a saturated methanol/hydrochloric acid mixture in 50 ml aliquots over 5 days. The methanol/hydrochloric acid is then removed under reduced pressure and the residue is carefully treated with aqueous sodium bicarbonate. When the aqueous layer tests basic, the solid is collected, washed with water, and dried under reduced pressure to give methyl 2-hydroxyquinoline-4-carboxylate (VI), mp 240°–241°.

Step II. Pyrrolidino 2-hydroxyquinoline-4-carboxamide (VI)

A mixture of methyl 2-hydroxyquinoline-4-carboxylate (VI, 0.286 g) and pyrrolidine (1.5 ml) in THF (2 ml) is heated at 80° for 3 hr, then at 20°–25° overnight. The mixture is then partitioned between dichloromethane and water. The organic phases are dried over sodium sulfate and concentrated to give pyrrolidino 2-hydroxyquinoline-4-carboxamide (VI), mp 221°–222°; upon crystallization from dichloromethane-acetone, mp 227°–229°.

Step III. Pyrrolidino 3-(5-cyclopropyl-1,2,4-oxadiazol-3-yl)imidazo[1,5-a]quinoline-5carboxamide (I)

To pyrrolidino 2-hydroxyquinoline-4-carboxamide (VI, 0.313 g) in dry DMF (2.5 ml) cooled at 0° are added dropwise over 5 min potassium tert-butoxide in THF (1M, 1.42 ml). The ice bath is removed and the mixture stirred for 25 min and then cooled again at 0°. Diethyl chlorophosphate (0.205 ml) is added and after stirring for 30 min the mixture is allowed to warm to 20°–25©. After 30 min at 20°–25° the mixture (containing intermediate VII) is cooled again at 0° and 3-isocyanomethyl-5-cyclopropyl-1,2,4-oxadiazole (IX, 0.231 g) is added, followed by potassium tert-butoxide in THF (1M, 1.55 ml). The mixture is stirred overnight at 5° and then partitioned between ethyl acetate and saline. The organic layers are dried over magnesium sulfate and concentrated. The crude product is chromatographed (silica gel; methanol (20%)/dichloromethane(80%)//ethyl acetate (2/98)), to give the title compound. Crystallization from dichloromethane/ethyl acetate/hexane provides the title compound, mp 233°–235°; MS (m/z) at 373; IR (mineral oil) 1566, 1638, 1625, 1476 and 3086 $cm^{-1}$.

Example 2

Dimethylamino 3-(5-cyclopropyl-1,2,4-oxadiazol-3-yl)-imidazo[1,5-a]quinoline-5-carboxamide (I)

Step I. 2-Hydroxyquinolin-4-oyl chloride (V-A)

A mixture of 2-hydroxyquinoline-4-carboxylic acid (V. 2.89 g) and of thionyl chloride (25 ml) is stirred at 80° for 12 hr and then allowed to cool. Excess thionyl chloride is removed under reduced pressure and dichloromethane is added to the residue. The dichloromethane is then removed and the process repeated to remove traces of thionyl chloride. The residue is dried under reduced pressure to give 2-hydroxyquinolin-4-oyl chloride (V-A) as a solid, which is used without further purification, mp: shrinkage and melting from approximately 260°–275°.

Step II. Dimethylamino 2-hydroxyquinoline-4-carboxamide (VI)

To 2-hydroxyquinolin-4-oyl chloride (V-A, 0.90 g) in dichloromethane (20 ml) are added dimethylamine hydrochloride (0.52 g), followed by diisopropylethylamine (1.12 ml). After stirring for 5 hr aqueous sodium bicarbonate is added and the mixture is extracted several times with dichloromethane. The organic layers are dried over sodium sulfate and concentrated. The crude product was chromatographed (silica gel; methanol/dichloromethane (2/98 to 4/96)), to give dimethylamino 2-hydroxyquinoline-4-carboxamide (VI, 0.73 g), mp 219°–220°.

Step III. Dimethylamino 3-(5-cyclopropyl-1,2,4-oxadiazol-3-yl)-imidazo[1,5-a]quinoline-5-carboxamide (I)

Following the general procedure of EXAMPLE 1 (Step III) and making non-critical variations but using dimethylamino 2-hydroxyquinoline-4-carboxamide (VI, 0.73 g), the title compound is obtained, mp 235.0°–235.5° (after crystallization from dichloromethane/hexane); MS (m/z) at 347; IR (mineral oil) 1624, 1568, 758, 1409 and 771 $cm^{-1}$.

Example 3 tert-Butyl 4-[(pyrrolidino)carbonyl]imidazo[1,5-a]quinoline-3-carboxylate (I)

Step I. Pyrrolidino 2-trifluoromethanesulfonatoquinoline-4-carboxamide (VIII)

To pyrrolidino 2-hydroxyquinoline-4-carboxamide (VI. EXAMPLE 1—Step I, 5.00 g) and pyridine (1.84 ml) in dichloromethane (35 ml) at 0° is added trifluoromethanesulfonic anhydride (3.82 ml). The mixture is allowed to warm slowly to 20°–25° while stirring overnight. Partitioning between dichloromethane, water, and saline, followed by drying over sodium sulfate and by chromatography (silica gel; ethyl acetate/dichloromethane (15/85)), a gum is obtained which is crystallized from ether to give pyrrolidino 2-trifluoromethanesulfonatoquinoline-4-carboxamide (VIII), mp 94°–96°.

Step II. tert-Butyl 4-[(pyrrolidino)carbonyl]imidazo[1.5-a] quinoline-3-carboxylate (I)

To tert-butyl isocyanoacetate (IX, 0.662 g) in THF (10 ml) cooled at −78° are added potassium tert-butoxide in THF (1M, 4.69 ml). After stirring for 20 min, pyrrolidino 2-trifluoromethanesulfonatoquinoline-4-carboxamide (VIII, Step I, 1.596 g) in THF (5 ml) are added. The mixture is stirred at −78° for 5 hr, then allowed to slowly warm to 20°–25° over 1 hr. The mixture is then quenched with several drops of acetic acid and partitioned between ethyl acetate and saline. The organic layers are dried over magnesium sulfate, concentrated, and chromatographed (silica gel methanol/dichloromethane (4/96)). Crystallization from dichloromethane/hexane gives the title compound, mp 216.5°–217.5° ; MS (m/z) at 365; IR (mineral oil) 1630, 1688, 1128, 1454 and 1159 $cm^{-1}$.

Example 4

Pyrrolidino 3-[5-(1-methylethyl)-1,2,4-oxadiazol-3-yl]imidazo[1,5a]quinoline-5-carboxamide (I)

Following the general procedure of EXAMPLE 3 (Step II) and making non-critical variations pyrrolidino 2-trifluoromethanesulfonatoquinoline-4-carboxamide (VIII, EXAMPLE 3—Step I, 1.446 g) and 3-isocyanomethyl-5-(1-methylethyl)-1,2,4-oxadiazole (IX, 0.642 g) are converted to the title compound, mp 225°–227° ; MS (m/z) at 375; IR (mineral oil) 1569, 1637, 1625, 1455 and 1443 $cm^{-1}$.

Example 5

Pyrrolidino 3-[5-(1,1-dimethylethyl)-1,2,4-oxadiazol-3-yl]imidazo[1,5-a]quinoline-5-carboxamide (I)

Following the general procedure of EXAMPLE 3 (Step II) and making non-critical variations pyrrolidino 2-trifluoromethanesulfonatoquinoline-4-carboxamide (VIII, EXAMPLE 3—Step I 1.104 g) and 5-(1,1-dimethylethyl)-3-isocyanomethyl-1,2,4-oxadiazole (IX, 0.487 g) are converted to the title compound, mp 228°–229°; MS (FAB, m+H) at 390; IR (mineral oil) 1625, 1584, 1476, 1606 and 1432 $cm^{-1}$.

Example 6

Pyrrolidino 3-phenylimidazo[1,5-a]quinoline-5-carboxamide (I)

A mixture of pyrrolidino 2-trifluoromethanesulfonatoquinoline-4-carboxamide (VIII, EXAMPLE 3—Step I, 0.882 g) and benzyl isocyanide (IX, 0.331 g) in THF (4 ml) is stirred at −78°. To this is added dropwise over 10 min potassium tert-butoxide in THF (1M, 2.83 ml). After stirring for 40 min at −78°, the mixture is quenched with several drops of acetic acid. The mixture is partitioned between ethyl acetate and saline and the organic layers are dried over magnesium sulfate and concentrated. The residue is chromatographed (silica gel; methanol/dichloromethane (2/98)) to give a solid which is recrystallized from dichloromethane/ether/hexane to give the title compound, mp 188°–191°; MS (m/z) at 341; IR (mineral oil) 1613, 1440, 1597, 1482 and 1435 cm$^{-1}$.

Example 7

Morpholino 3-(5-cyclopropyl-1,2,4-oxadiazol-3-yl)imidazo[1,5-a]quinoline-5-carboxamide (I)

Step I. Morpholino 2-hydroxyquinoline-4-carboxamide (VI)

Following the general procedure of EXAMPLE 2 (Step II) and making non-critical variations 2-hydroxyquinoline-4-oyl chloride (V-A, EXAMPLE 2, Step I, 0.947 g) and morpholine (2 ml) give morpholino 2-hydroxyquinoline-4-carboxamide (VI), mp 193°–194°.

Step II. Morpholino 3-(5-cyclopropyl-1,2,4-oxadiazol-3-yl)imidazo[1,5-a]quinoline-5-carboxamide (I)

To morpholino 2-hydroxyquinoline-4-carboxamide (VI, Step I, 0.47 g) in THF (15 ml) and dry DMF (2 ml) cooled at −15° is added potassium tert-butoxide in THF (1M, 1.82 ml). The mixture is stirred for 15 min, after which p-toluenesulfonyl chloride (0.347 g) is added. After stirring for 40 min. 5-cyclopropyl-3-isocyanomethyl-1,2,4-oxadiazole (IX, 0.300 g) is added, followed by potassium tert-butoxide (1M, 2.00 ml). The mixture is stirred an for additional 2 hr, quenched with several drops of aqueous sodium bicarbonate, and taken to dryness under reduced pressure. The residue is chromatographed (silica gel; methanol/dichloromethane (2/98)) to give the product, which is crystallized from dichloromethane/ether/hexane to give the title compound, mp 250°–252°; MS (m/z) at 389; IR 1628, 1584, 1115, 1249 and 1274 cm$^{-1}$.

Example 8 tert-Butyl 4-methyl-5-[(pyrrolidino)carbonyl]imidazo[1,5-a]quinoline-3-carboxylate (I)

Step I. Isatin propionamide (IV)

A mixture of isatin (III, 10.206 g), propionic anhydride (10.83 ml) and THF (25 ml) is stirred at 80° for 24 hr, after which an additional propionic anhydride (1 ml) is added. The mixture is stirred for another 12 hr at 80°, after which the solvent is removed under reduced pressure and the residue is partitioned between dichloromethane and water. The organic layers are dried over sodium sulfate and concentrated. Recrystallization from ether and hexane gives isatin propionamide (IV), mp 139°–140°; NMR (CDCl$_3$) 1.28, 3.15, 7.34, 7.72, 7.78 and 8.45 δ.

Step II. 2-Hydroxy-3-methylquinoline-4-carboxylic acid (V)

A mixture of isatin propionamide (IV, Step I, 10.16 g) in potassium hydroxide (1N, 150 ml) is stirred at 100° for 6.5 hr. The mixture is then cooled and adjusted to pH 5 with concentrated hydrochloric acid. Sodium chloride is added to saturate the mixture, which is then washed twice with ethyl acetate and discarded. The aqueous layer is concentrated to about half volume and the solid is collected and dried to give 2-hydroxy-3-methylquinoline-4-carboxylic acid (V), mp >310°; NMR (DMSO-d6) 1.96, 7.05, 7.21, 7.33, 7.52 and 11.42 δ.

Step III. Pyrrolidino 2-hydroxy-3-methylquinoline-4-carboxamide (VI)

A mixture of 2-hydroxy-3-methylquinoline-4-carboxylic acid (V, Step II, 5.11 g) and thionyl chloride (35 ml) is stirred at reflux for 3.5 hr. After cooling, the excess thionyl chloride is removed under reduced pressure. The residue is taken up in dichloromethane and taken to dryness again under reduced pressure. The dichloromethane addition/removal under reduced pressure is repeated twice. The residue is then dried under greatly reduced pressure for 1 hr to remove the last traces of thionyl chloride to give 2-hydroxy-3-methylquinolin-4-oyl chloride (V-A), which is taken up in 30 to 40 ml of dichloromethane and cooled at 0°. Triethylamine (3.50 ml) is added, followed by pyrrolidine (4.19 ml). After 5–10 min the ice bath is removed. After stirring for 3 hr, the mixture is partitioned between dichloromethane and aqueous sodium bicarbonate. The mixture is filtered through sodium sulfate and concentrated to a residue. The residue is chromatographed (silica gel; methanol/dichloromethane (4/96)) to give pyrrolidino 2-hydroxy-3-methylquinoline-4-carboxamide (VI), mp 175°–176° which is crystallized from acetone, mp 223°–227°.

Step IV. Pyrrolidino 3-methyl-2-trifluoromethanesulfonatoquinoline-4-carboxamide (VIII)

A mixture of pyrrolidino 2-hydroxy-3-methylquinoline-4-carboxamide (VI, Step III, 4.64 g), pyridine (1.61 ml) and dichloromethane (35 ml) is stirred at 0°. Trifluoromethanesulfonic anhydride (3.35 ml) is added to this mixture. The mixture is allowed to slowly warm to 20°–25° while stirring overnight, then partitioned between dichloromethane and water and the organic layers dried over sodium sulfate. The crude material is chromatographed (silica gel; ethyl acetate/dichloromethane (10/90)) to give pyrrolidino 3-methyl-2-trifluoromethanesulfonatoquinoline-4-carboxamide (VIII) as a gum which solidified upon the addition of ether; mp 111°–112°.

Step V. tert-Butyl 4-methyl-5-[(pyrrolidino)carbonyl]imidazo[1,5-a]quinoline-3-carboxylate (I)

Potassium tert-butoxide (1M in THF, 5.96 ml) is added to a mixture of tert-butyl isocyanoacetate (IX, 0.84 g) in THF (10 ml) cooled at −78°. After stirring for 30 min, a mixture of pyrrolidino 3-methyl-2-trifluoromethanesulfonatoquinoline-4-carboxamide (VIII, Step IV, 1.93 g) in THF (10 ml) is added. After 5 hr of stirring at −78°, the mixture is allowed to warm to 20°–25°. After storing in the freezer over the weekend, the mixture is partitioned between chloroform and saline. The organic phase is dried over sodium sulfate and concentrated. The concentrate is chromatographed (silica gel; methanol/dichloromethane (2/98)) to give, after crystallization from dichloromethane/ethyl ether/hexane, the title compound, mp 206.0°–207.5°; MS (m/z) at 379; IR (mineral oil) 1640, 1128, 1440, 1714 and 1034 cm$^{-1}$.

Example 9

Pyrrolidino
4-methyl-3-[5-(1-methylethyl)-1,2,4-oxadiazol-3-yl]imidazo [1,5-a]quinoline-5-carboxamide (I)

Following the general procedure of EXAMPLE 8, Step V and making non-critical variations but starting with 3-methyl-2-trifluoromethanesulfonatoquinoline-4-(pyrrolidino)carboxamide (VIII, EXAMPLE 8, Step IV) and 3-isocyanomethyl-5-(1-methylethyl)-1,2,4-oxadiazole (IX, 0.88 g) are converted to the product; crystallization from dichloromethane/hexane, followed by recrystallization from ethyl acetate, gives the title compound, mp 173°–174°; MS (m/z) at 389; IR (mineral oil) 1621, 1580, 759, 1481 and 1445 cm$^{-1}$.

Example 10

Dimethylamino
3-(5-cyclopropyl-1,2,4-oxadiazol-3-yl)-4-methylimidazo-[1,5-a]quinoline-5-carboxamide (I)

Step I. Dimethylamino 2-hydroxy-3-methylquinoline-4-carboxamide (VI)

Diisopropylethylamine (0.82 ml) is added to a mixture of 2-hydroxy-3-methylquinolin-4-oyl chloride (V-A, EXAMPLE 8, Step III, 0.521 g) and dimethylamine hydrochloride (0.383 g) in dichloromethane (4 ml). After 1.5 hr the mixture is partitioned between dichloromethane and water. The organic phase is dried over sodium sulfate, concentrated, and chromatographed (silica gel; ethyl acetate) to give dimethylamino 2-hydroxy-3-methylquinoline-4-carboxamide (VI). An aliquot crystallized from dichloromethane/hexane is mp 187°–188°.

Step II. Dimethylamino 3-(5-cyclopropyl-1,2,4-oxadiazol-3-yl)-4-methylimidazo[1,5-a]quinoline-5-carboxamide (I)
Potassium tert-butoxide (1M in THF, 2.20 ml) is added to dimethylamino 2-hydroxy-3-methylquinoline-4-carboxamide (VI, 0.483 g) in THF (12 ml) cooled at –10°. After stirring for 25 min, diethyl chlorophosphate (0.32 ml) is added. The mixture is stirred at –10 to 0° for 1 hr, after which 5-cyclopropyl-3-isocyanomethyl-1,2,4-oxadiazole (IX, 0.344 g) is added, followed by potassium tert-butoxide (1M in THF, 2.31 ml). The mixture is stirred at 0° for 4 hr, after which the solvent is removed under reduced pressure and the residue is partitioned between dichloromethane and aqueous sodium bicarbonate. The organic phase is dried over sodium sulfate and concentrated. The residue is chromatographed (silica gel; methanol/dichloromethane (2/98)) and crystallized from dichloromethane/hexane to give dimethylamino 3-(5-cyclopropyl=1,2,4-oxadiazol-3-yl)-4-methylimidazo[1,5-a]quinoline-5-carboxamide, mp 190°–192°; MS (m/z) at 361; IR 1630, 1564, 755, 1410 and 1449 cm$^{-1}$.

Example 11

Pyrrolidino
3-(5-cyclopropyl-1,2,4-oxadiazol-3-yl)-4-methylimidazo[1,5-a]quinoline-5-carboxamide (I)

Following the general procedure of EXAMPLE 8 and making non-critical variations but starting with pyrrolidino 2-hydroxy-3-methylquinoline-4-carboxamide (VI, 0.555 g), the title compound is obtained, mp 206°–209°; MS (m/z) at 387; R (mineral oil) 1634, 1557, 1623, 1447 and 1476 cm$^{-1}$.

Example 12

Morpholino
3-(5-cyclopropyl-1,2,4-oxadiazol-3-yl)-7-fluoroimidazo[1,5-a]quinoline-5-carboxamide (I)

Step I. 5-Fluoroisatin acetamide (IV)

A mixture of 5-fluoroisatin (III, 0.803 g), acetic anhydride (0.546 g), dimethylaminopyridine (0.0059 g) and THF (25 ml) is stirred at 20°–25° for 1.25 hr. THF is then removed and dichloromethane is added. After standing, the crystals are collected and dried to give 5-fluoroisatin acetamide (IV).
Step II. Morpholino 6-fluoro-2-hydroxyquinoline-4-carboxamide (VI).

A mixture of 5-fluoroisatin acetamide (IV), THF (2 ml), and 1N potassium hydroxide (7.9 ml) is stirred at 95° while allowing the THF to distill off. After 1.5 hrs the mixture is removed is from the heating bath and is concentrated under reduced pressure. Hydrochloric acid (4N, 1.9 ml) is added, and the mixture is again concentrated to dryness under reduced pressure. The residue (V) is then stirred at reflux in thionyl chloride (10 ml) for 3.5 hrs, after which it is cooled and excess thionyl chloride is removed under reduced pressure. Dichloromethane is added and again the mixture is taken to dryness under reduced pressure to remove any residual thionyl chloride. To the solid is then added dichloromethane (10 ml) and the mixture is stirred at ice bath temperature. Diisopropylethylamine (0.55 ml) is added, followed by morpholine (0.55 ml). The ice bath is then removed and the mixture is stirred at 20°–25° for 30 min, at which time the mixture is partitioned between dichloromethane and aqueous sodium bicarbonate. The organic phases are dried over sodium sulfate, concentrated, and the residue chromatographed (silica gel; methanol/dichloromethane (2/98 to 4/96)) to give morpholino 6- fluoro-2-hydroxyquinoline-4-carboxamide (VI); mp 260°–261°; MS m/z at 276; IR (mineral oil) 1665, 1633, 1424, 1253, 1119, 1450 cm$^{-1}$.
Step III. Morpholino 6-fluoro-2-trifluoromethanesulfonatoquinoline-4-carboxamide (VIII)

Following the general procedure of EXAMPLE 3 Step I and making non-critical variations but starting with morpholino 6-fluoro-2-hydroxyquinoline-4 carboxamide (VI), morpholino 6-fluoro-2-trifluoromethanesulfonatoquinoline-4-carboxamide (VIII) is obtained.
Step IV. Morpholino 3-(5-cyclopropyl-1,2,4-oxadiazol-3-yl)-7-fluoroimidazo[1,5-a]quinoline-5-carboxamide (I)

Following the general procedure of EXAMPLE 3, Step II and making non-critical variations but starting with morpholino 6-fluoro-2-trifluoromethanesulfonatoquinoline-4-carboxamide (VIII, Step III) the title compound is obtained, mp 245°–246.5°; IR (mineral oil) 1630, 1476, 1583, 1203 and 1104 cm$^{-1}$.

Example 13 tert-Butyl
5-[(cis-3,5-dimethylpiperazino)carbonyl]imidazo[1,5-a]quinoline-3-carboxylate (I)

Step I. cis-3,5-Dimethylpiperazino 2-chloroquinoline-4-carboxamide (X)

A mixture of 2-hydroxyquinoline-4-carboxylic acid (V, 1.25 g), thionyl chloride (8.3 ml) and DMF (1 drop) is heated at reflux for 1 hr. The resultant mixture is allowed to cool to 20°–25° and is concentrated. Toluene (25 ml) is added and the mixture concentrated. cis-2,6-Dimethylpiperazine (906 mg) is added to a mixture of the crude acid chloride, methylene chloride (35 ml) and diisopropylethylamine (1.66 ml) at 0°. The mixture is stirred for 1 hr at 0° and for 16 hrs at 20°–25°. Partitioning between methylene chloride and sodium bicarbonate, drying of the combined organic phase over magnesium sulfate, filtration, concentration, and crystallization from ether/hexane gives 3,5-dimethylpiperazino 2-chloroquinoline-4-carboxamide (X), mp 305° dec: IR (mineral oil) 1646, 1639, 1556, 1445, 1098, 774 cm$^{-1}$; NMR (CDCl$_3$) 8.08, 7.55–7.95, 7.2–7.4. 4.7–4.9, 2.4–3.2, 1.5–1.9, 1.15–1.35, 0.93 and 0.87 δ; MS (EI, m/e)303, 259, 207, 190, 162, 127, 113, 101 and 84.

Step II. tert-Butyl 5-[(cis-3,5-dimethylpiperazino)carbonyl]imidazo[1,5-a]quinoline-3-carboxylate (I)

Potassium tert-butoxide (2.6 ml, 1.0M in THF) is added to a mixture of cis-3,5-dimethylpiperazino 2-chloroquinoline-4-carboxamide (X, 704 mg ), tert-butyl isocyanoacetate (IX. 390 mg ) and DMF (10 ml) at −78°. The mixture is stirred for 1 hr at −78° and is allowed to warm to 20°–25° over several hours. After stirring at 20°–25° for 16 hrs, water is added and the mixture extracted several times with ethyl acetate, the combined organic phases are dried over magnesium sulfate, filtered, and concentrated to provide a mixture of product and starting material, which is resubmitted to the above conditions (THF used instead of DMF). Purification of the resultant crude material by flash chromatography (silica gel; ethyl acetate/methanol (4/1)) provides the product. Recrystallization from hot ethyl acetate/hexane gives the desired title compound, mp 233°–234°; IR (mineral oil) 1719, 1615, 1607, 1388, 1270, 1128 cm$^{-1}$; NMR (CDCl$_3$) 8.67, 7.95–8.15, 7.65–7.9, 7.54, 4.7–4.85, 3.35–3.55, 2.4–3.1, 1.68, 1.22 and 0.85–1.05 δ; MS (EI, m/e) 408, 351, 335, 307, 239, 195 and 113.

Example 14 tert-Butyl 7-fluoro-5-[(3,5-dimethylpiperazino)carbonyl]imidazo[1,5-a]quinoline-3-carboxylate (I)

Step I. 5-Fluoroisatin acetamide (IV)

4-Dimethylaminopyridine (0.296 g) is added to a mixture of 5-fluoroisatin (III, 10.0 g), acetic anhydride (6.29 ml) and THF (90.0 ml). The reaction mixture is stirred at 20°–25° for 1.25 hrs. Concentration and trituration (ether, methylene chloride/hexane (1/1)) gives 5-fluoroisatin acetamide (IV), mp 142°–144°; IR (mineral oil) 1781, 1753, 1713, 1707, 1478, 1325, 1299, 1234, 1164 and 852 cm$^{-1}$; NMR (CDCl$_3$) 8.45–8.55, 7.35–7.5 and 2.74 δ; MS (EI, m/e) 207, 165, 164, 108 and 43.

Step II. 6—Fluoro-2-hydroxyquinoline-4-carboxylic acid (V)

Potassium hydroxide (1N, 100.0 ml) is added to a mixture of 5-fluoroisatin acetamide (IV, 8.44 g) and THF (33 ml). The mixture is heated at reflux for 1 hr, allowing the THF to distill off. The mixture is then cooled to 5° and is extracted with methylene chloride (3×50 ml). The basic layer is neutralized with hydrochloric acid (4N, 16.3 ml) and the resulting solids collected and washed with water (200 ml) and methylene chloride (100 ml) to give 6-fluoro-2-hydroxyquinoline-4-carboxylic acid (V), mp >293°; IR (mineral oil) 1714, 1648, 1623, 1508, 1436, 1261, 1255, 1244, 1234 and 1222 cm$^{-1}$; NMR (d$_6$-DMSO) 12.20, 8.04, 7.35–7.60 and 7.00 δ; MS (EI, m/e) 207, 162, 135 and 107.

Step III. cis-3,5-Dimethylpiperazino 2-chloro-6-fluoroquinoline-4-carboxamide (X)

DMF (2 drops) is added to a suspension of 6-fluoro-2-hydroxyquinoline-4-carboxylic acid (V, 1.25 g) and thionyl chloride (7.6 ml) and the mixture heated at reflux for 1 hr. After cooling to 20°–25°, the mixture is concentrated and diluted with toluene and concentrated several times to remove any excess thionyl chloride. The crude is used without further purification. cis-2,6-Dimethylpiperazine (0.76 g) is added to a mixture of the acid chloride, methylene chloride (30 ml), and diisopropylethylamine (1.44 ml). The mixture is stirred at 0° for 1 hr and at 20°–25° for 17 hrs. Partitioning of the residue between sodium bicarbonate and methylene chloride, drying of the combined organic layers over sodium sulfate, filtration, concentration, and purification by flash chromatography (silica gel; methanol/ethyl acetate (5/95)) gives cis-3,5-dimethylpiperazino 2-chloro-6-fluoroquinoline-4-carboxamide (X), mp 133°–134°; IR (mineral oil) 1631, 1560, 1445, 1320, 1295, 1264, 1226, 1140, 1096 and 830 cm$^{-1}$; NMR (CDCl$_3$) 8.07, 7.2–7.65, 4.65–4.85, 2.5–3.2, 1.58, 1.20, 0.94 and 0.89 a: MS (EI, m/e) 321,277, 208, 180, 145, 113,84 and 70.

Step IV. tert-Butyl 7-fluoro-5-[(cis-3,5-dimethylpiperazino)carbonyl]imidazo[1,5a]quinoline-3-carboxylate (I)

Potassium tert-butoxide (1.0M in THF, 5.3 ml) is slowly added to a mixture of the cis-3,5-dimethylpiperazino-2-chloro-6-fluoroquinoline-4-carboxamide (X, 1.50 g), tert-butyl isocyanoacetate (IX 0.82 g) and THF (19 ml) at −78°. The mixture is stirred at −78° for 1 hr and is allowed to warm to 20°–25°. After stirring at 20°–25° for 26 hrs the reaction is quenched with water (20 ml). The mixture is extracted several times with methylene chloride, the combined organic phases are dried over sodium sulfate, filtered, concentrated, and purified by crystallization (ethyl acetate/ hexane) to give the title compound, mp 198°–199°; IR (mineral oil) 1718, 1618, 1568, 1480, 1441, 1394, 1271, 1152, 1140 and 1128 cm$^{-1}$; NMR (CDCl$_3$) 8.62, 8.0–8.15, 7.3–7.6, 4.7–4.85, 3.35–3.55, 2.4–3.1, 1.68, 1.20 and 0.85–1.0 δ; MS (EI, m/e) 426, 369, 353, 325, 213, 113, 72 and 70.

Example 15 tert-Butyl 7-chloro-5-[(cis-3,5-dimethylpiperazino)carbonyl]imidazo-[1,5-a]quinoline-3-carboxylate (I)

Step I. 5-Chloroisatin acetamide (IV)

Solid 4-dimethylaminopyridine (102 mg) is added to a stirred mixture of 5-chloroisatin (III, 3.80 g), acetic anhydride (2.2 ml) and THF (30 ml) at 20°–25°. The resulting mixture is stirred for 1 hr. The mixture is concentrated, methylene chloride (30 ml) is added, and the mixture is again concentrated. The solids are triturated for 30 min in methylene chloride (30 ml), filtered, washed with methylene chloride/hexane (1/1) and dried to give 5-chloroisatin acetamide (IV), mp 162°–164°. The filtrate is concentrated, the solids are triturated for 30 min in methylene chloride (15 ml), filtered, and washed with methylene chloride/hexane (1/1) to provide additional product. IR (mineral oil) 1765, 1749, 1721, 1599, 1308, 1290, 1260 and 1163 cm$^{-1}$: NMR (CDCl$_3$) 8.42, 7.75, 7.69 and 2.75 δ; MS (EI, m/e) 223, 180, 153 and 124.

Step II. 6-Chloro-2-hydroxyquinoline-4-carboxylic acid (V)

A mixture of 5-chloroisatin acetamide (IV, 5.00 g), potassium hydroxide (1N, 56 ml) and THF (18 ml) is heated at reflux for 1 hr, allowing the THF to boil off, and is allowed to cool to 20°–25°. The basic mixture is cooled to 0° and acidified to pH 5.5 (pH paper) with hydrochloric acid (4N).

The resulting solids are filtered, washed with water and methylene chloride, dried, and triturated overnight in methylene chloride (200 ml, to remove a small amount of 5-chloroisatin byproduct). These solids are filtered, washed with methylene chloride, and dried to give 6-chloro-2-hydroxyquinoline-4-carboxylic acid (V), mp >300°; IR (mineral oil) 1711, 1645, 1430, 1221,1179, 887 and 881 cm$^{-1}$; NMR (d$_6$-DMSO) 12.25,8.30, 7.62, 7.38 and 7.00 δ; MS (EI, m/e) 223, 178 and 151.

Step II. (Alternative Procedure) 6-Chloro-2-hydroxyquinoline-4-carboxylic acid (V)

A mixture of 5-chloroisatin (III, 1.00 g), malonic acid (0.860 g), and THF (15 ml) is heated at reflux for 16 hr. The resultant mixture is allowed to cool to 20°–25° and is concentrated to give a solid which was carried on crude, NMR (d$_6$-DMSO) 7.41, 7.24, 6.79, 6.20, 2.96 δ. The residue is combined with water (20 ml) and the mixture heated at reflux for 6 hr before being allowed to cool to 20°–25°. The precipitate is filtered, washed and dried to give the title compound which has identical spectral data to that reported above (Step II).

Step III. cis-3,5-Dimethylpiperazino 2,6-dichloroquinoline-4-carboxamide (X)

A mixture of the finely-ground 6-chloro-2-hydroxyquinoline-4-carboxylic acid (V, 2.44 g), thionyl chloride (40 ml) and DMF (2 drops) is heated at reflux for 1 hr and allowed to cool to 20°–25. Toluene (50 ml) is added and the mixture is concentrated; twice more toluene (50 ml) is added and the mixture concentrated. The acid chloride is slurried in methylene chloride (25 ml) and added dropwise to a stirred mixture of cis-2,6-dimethylpiperazine (1.62 g), diisopropylethylamine (2.9 ml) and methylene chloride (50 ml) at 0°. The mixture is allowed to warm slowly and is stirred overnight at 20°–25°. Water (5 ml) is added and the mixture concentrated. Partitioning of the residue between ethyl acetate and sodium bicarbonate, drying of the combined organic layers over magnesium sulfate, filtration, concentration and purification by flash chromatography (methanol/methylene chloride (5/95), with 0.5% ammonium hydroxide), gives a solid. Recrystallization from ethyl acetate/hexane gives cis-3,5-dimethylpiperazino2,6-dichloroquinoline-4-carboxamide (X), mp 169°–170°; IR (mineral oil) 1644, 1431, 1100, 888 and 826 cm$^{-1}$; NMR (CDCl$_3$) 8.01, 7.6–7.9, 7.2–7.4, 4.65–4.85, 2.4–3.2, 1.56, 1.1–1.35 and 0.8–1.05 δ; MS (EI, m/e) 337, 293, 224, 196, 161,127, 113, 99, 84, 70 and 41.

Step IV. tert-Butyl 7-chloro-5-[(cis-3,5-dimethylpiperazino)carbonyl]-imidazo[1,5a]quinoline-3-carboxylate (I)

A mixture of cis-3,5-dimethylpiperazino 2,6-dichloroquinoline-4-carboxamide (X, 1.20 g) and THF (18 ml) is cooled to −78°. tert-Butyl isocyanoacetate (IX, 0.65 ml) is added followed by potassium tert-butoxide (1.0N in THF, 4.4 ml), which is added dropwise over several minutes. The mixture is allowed to warm slowly and is stirred for 4 days at 20°–25°. The mixture is quenched with water (5 ml) and the mixture is concentrated. The residue is partitioned between ethyl acetate and sodium bicarbonate, the combined organic layers dried over magnesium sulfate, filtered, concentrated, and purified by flash chromatography ((silica gel; methanol/ethyl acetate (15/85)) to give a solid. Recrystallization from ethyl acetate/hexane gives the title compound, mp 208°–210°; IR (mineral oil) 1689, 1638, 1262, 1256. 1158, 1136 and 814 cm$^{-1}$; NMR (CDCl$_3$) 8.63, 8.09, 8.0–8.1, 7.81, 7.6–7.7, 4.65–4.85, 3.35–3.55, 2.4–3.1, 1.68, 1.21 and 0.9–1.05 δ; MS (EI, m/e) 442, 385, 369, 341, 315, 303, 273, 229, 174, 113, 84 and 72.

Example 16 tert-Butyl 7-chloro-5-[(3,3,5,5-tetramethylpiperazino)carbonyl]imidazo-[1,5-a]quinoline-3-carboxylate (I)

Step I. 3,3,5,5-Tetramethylpiperazino 2,6-dichloroquinoline-4-carboxamide (X)

A mixture of the finely ground 6-chloro-2-hydroxyquinoline-4-carboxylic acid (V, 408 mg), thionyl chloride (15 ml) and DMF (2 drops) is heated at reflux for 2 hrs and is allowed to cool to 20°–25°. Toluene (15 ml) is added and the mixture concentrated to give a solid which is concentrated twice more from toluene (15 ml). The acid chloride is dissolved in methylene chloride (15 ml) and added dropwise to a stirred mixture of 2,2,6,6-tetramethylpiperazine (*Bull. Chem. Soc. Jpn.* 45, 1855 (1972), 300 mg ), diisopropylethylamine (0.45 ml) and methylene chloride (15 ml) at 0°. The mixture is allowed to warm slowly and is stirred overnight at 20°–25°. Water (2 ml) is added and the mixture concentrated. The residue is partitioned between ethyl acetate and sodium bicarbonate, the combined organic phase is dried over magnesium sulfate, filtered, concentrated, and purified by flash chromatography (methanol/ethyl acetate, (10/90)) to give 3,3,5,5-tetramethylpiperazino 2,6-dichloroquinoline-4-carboxamide (X), mp 171°–172°; IR (mineral oil) 3312, 1630, 1451, 1431, 1265, 886, 877 and 827 cm$^{-1}$; NMR (CDCl$_3$) 8.01, 7.7–7.8, 7.36, 3.64, 2.94, 1.31, 1.30, 1.12 and 0.95 δ; MS (EI, m/e) 365, 307, 224, 196, 161, 98, 84, 58 and 41.

Step II. tert-Butyl 7-chloro-5-[(3,3,5,5-tetramethylpiperazino)carbonyl]imidazo[1,5-a]quinoline-3-carboxylate (I)

A mixture of 3,3,5,5-tetramethylpiperazino 2,6-dichloroquinoline-4-carboxamide (X, 310 mg ) and THF (5 ml) is cooled to −78°. tert-Butyl isocyanoacetate (IX, 0.148 ml) is added followed by potassium tert-butoxide (1.0N in THF, 1 ml), which is added dropwise over several min. The mixture is allowed to warm slowly and is stirred for 3 days at 20°–25°. The residue is partitioned between ethyl acetate and sodium bicarbonate, the combined organic layers dried over magnesium sulfate, filtered, concentrated, and triturated in ether to give a solid which is purified by flash chromatography (silica gel; methanol/ethyl acetate (5/95)). Recrystallization from ethyl acetate/hexane gives the title compound. The mother-liquors of the trituration and the recrystallization are combined, purified by flash chromatography (same system), and recrystallized from ether/hexane to give additional product, mp 241°–242°; IR (mineral oil) 1694, 1642, 1421, 1393, 1172, 1159 and 1133 cm$^{-1}$; NMR (CDCl$_3$) 8.63, 8.07, 8.03, 7.74, 7.66, 3.5–3.75, 3.15, 1.66, 1.31, 1.17 and 0.99 δ; MS (EI, m/e) 470, 413, 397, 369, 356, 338, 312, 273, 229, 201, 174, 155, 98, 84 and 58.

Example 17 tert-Butyl 7-chloro-5-[(piperazino)carbonyl]imidazo[1,5-a]quinoline-3-carboxylate (I)

Step I. [4-(tert-Butyloxycarbonyl)piperazino]2,6-dichloroquinoline-4-carboxamide (X)

A mixture of the finely ground 6-chloro-2-hydroxyquinoline-4-carboxylic acid (V, 2.00 g), thionyl chloride (40 ml) and DMF (2 drops) is heated at reflux for 2 hrs. After cooling to 20°–25°, the remaining solids are removed by filtration. Toluene (40 ml) is added to the filtrate which is concentrated to give a yellow solid (which is concentrated twice more from 40 ml of toluene). A mixture of the acid chloride, diisopropylethylamine (2.3 ml) and methylene chloride (60 ml) is cooled to 0°. tert-Butyl 1-piperazinecarboxylate (2.00 g) is added in portions over a few minutes. The mixture is allowed to warm slowly and is stirred overnight at 20°–25°. Water (5 ml) is added and the mixture concentrated. The residue is partitioned between ethyl acetate and sodium bicarbonate, the combined organic phase is dried over magnesium sulfate, filtered, concentrated, and recrystallized from hot ethyl acetate/hexane to give [4-(tert-butyloxycarbonyl)piperazino]2,6-dichloroquinoline-4-carboxamide (X), mp 180°–181°; IR (mineral oil) 1695, 1638, 1406, 1365, 1242, 1175, 1126 and 886 cm$^{-1}$; NMR (CDCl$_3$) 8.01, 7.7–7.8, 7.34. 3.8–4.0, 3.62, 3.3–3.45, 3.1–3.3 and 1.47 δ; MS (EI, m/e) 409, 353, 336, 309, 279, 266, 254, 224, 196, 161,135, 85, 69, 57 and 40.

Step II. tert-Butyl 7-chloro-5-[4-(tert-butyloxycarbonyl)piperazino]imidazo [1,5- a]quinoline-3-carboxylate (XII)

A mixture of [4-(tert-butyloxycarbonyl)piperazino]2,6-dichloroquinoline-4-carboxamide (X, 1.40 g) and THF (15 ml) is cooled to −78°. tert-Butyl isocyanoacetate (IX, 0.60 ml) is added, followed by potassium tert-butoxide (4.1 ml, 1.0N in THF), which is added dropwise over several minutes. The mixture is allowed to warm slowly and is stirred for 3 days at 20°–25°. The mixture is diluted with water (25 ml) and the THF is evaporated under reduced pressure. The resulting solids are filtered, washed with water, dissolved in methanol/methylene chloride (5/95) and dried over magnesium sulfate. Filtration and concentration gives crude tert-butyl 7-chloro-5-[4(tert-butyloxycarbonyl)piperazino]imidazo[1,5-a]quinoline-3-carboxylate (XII) which is used without further purification in the next step, IR (mineral oil) 1698, 1699, 1641, 1419, 1392, 1367, 1257, 1243, 1163 and 1136 cm$^{-1}$; NMR (CDCl$_3$) 8.63, 8.07, 8.04, 7.75, 7.66, 3.8–4.0, 3.3–3.7, 1.68 and 1.48 δ; MS (EI, m/e) 514, 273, 246, 229 and 85.

Step III. tert-Butyl 7-chloro-5-[(piperazino)carbonyl]imidazo[1,5-a]quinoline-3-carboxylate (I)

Trifluoroacetic acid (10 ml) is added dropwise to a mixture of tert-butyl 7-chloro-5-[4-(tert-butyloxycarbonyl)piperazino]imidazo [1,5-a]quinoline-3-carboxylate (XII, 1.76 g) in 10 ml of methylene chloride at 20°–25°. The mixture is stirred for 20 min and is concentrated. Partitioning of the mixture between ethyl acetate (50 ml) and saturated aqueous sodium bicarbonate (30 ml) produced a solid byproduct, which is removed by filtration. The organic layer is discarded, and sodium hydroxide (50%, 5 ml) is added to the aqueous layer, which is extracted several times with methylene chloride and then ethyl acetate. The combined organic layers are dried (magnesium sulfate), filtered, and concentrated to give a solid. Recrystallization from methanol/methylene chloride/ethyl acetate gives the title compound. The concentrated filtrate is purified by flash chromatography (methanol/ethyl acetate (5/95)) to give additional product. Recrystallization of the combined lots from ethyl acetate/hexane provides the title compound, mp 239°–240°; IR (mineral oil) 1674, 1623, 1442, 1394, 1304, 1168, 1163 and 1144 cm$^{-1}$; NMR (CDCl$_3$) 8.63, 8.0–8.1, 7.77, 7.65, 3.8–4.05, 3.3–3.55, 3.0–3.1, 2.7–2.95 and 1.68 δ; MS (EI, m/e) 414, 341,303, 290, 274, 246, 229, 202, 85, 56 and 44.

Example 18 tert-Butyl 7-chloro-5-[(4-cyclopropylpiperazino)carbonyl]imidazo[1,5-a]quinoline-3-carboxylate (I)

Step I. 4-Cyclopropylpiperazino 2,6-dichloroquinoline-4-carboxamide (X)

A mixture of 6-chloro-2-hydroxyquinoline-4-carboxylic acid (V, 1.25 g), thionyl chloride (7.0 ml) and DMF (1 drop) is heated at reflux for 1 hr. The resultant mixture is allowed to cool to 20°–25° and is concentrated. Toluene (20 ml) is added and the mixture concentrated. To a mixture of the crude acid chloride, methylene chloride (28 ml), and diisopropylethylamine (2.70 ml) at 0° is added 1-cyclopropylpiperazine dihydrochloride (1.45 g). The mixture is stirred for 1 hr at 0° and for 16 hrs at 20°–25°. The residue is partitioned between methylene chloride and sodium bicarbonate, the combined organic layers dried over magnesium sulfate, filtered, and concentrated. Trituration of the residue with ether/hexane and filtration gives 4-cyclopropylpiperazino 2,6-dichloroquinoline-4-carboxamide (X); mp 200°–202°; IR (mineral oil) 1639, 1432, 1361, 884 and 824 cm$^{-1}$; NMR (CDCl$_3$) 8.00, 7.78, 7.72, 7.34, 3.75–4.0, 3.0–3.3, 2.7–2.9, 2.4–2.65, 1.4–1.8 and 0.3–0.6 δ; MS (EI, m/e) 349, 224, 196, 161,135, 125 and 96.

Step II. tert-Butyl 6-chloro-5-[(4-cyclopropylpiperazino)carbonyl]imidazo[1,5-a]quinoline-3-carboxylate (I)

Potassium tert-butoxide (1.0M in THF, 3.7 ml) is added to a mixture of 4-cyclopropylpiperazino-2,6-dichloroquinoline-4-carboxamide (X, 1.24 g), tert-butyl isocyanoacetate (IX, 600 mg) and THF (12 ml) at −78°. The mixture is stirred for 1 hr at −78° and is allowed to warm to 20°–25° over several hours. After stirring at 20°–25° for 16 hrs, the residue is partitioned between water and methylene chloride, the combined organic phase is dried over magnesium sulfate, filtered, concentrated, and purified by flash chromatography (silica gel; ethyl acetate/hexane (2/1)) to give the title compound as a solid. An additional amount of a mixture of starting material and product is isolated which is recycled as above to provide an additional amount of product after chromatography. Recrystallization of the combined lob from hot ethyl acetate/hexane gives the title compound, mp 229°–233°; IR (mineral oil) 1694, 1643, 1473, 1441, 1423, 1391, 1367, 1253, 1159 and 1139 cm$^{-1}$; NMR (CDCl$_3$) 8.62, 8.06, 8.03, 7.77, 7.65.3.8–3.95, 3.25–3.5, 2.7–2.85.2.4–2.7, 1.68, 1.5–1.8 and 0.35–0.55 δ; MS (EI, m/e) 454, 273, 220, 124 and 96.

Example 19 tert-Butyl 7-chloro-5-[((3R)-methylpiperazino)carbonyl]imidazo[1,5-a]quinoline-3-carboxylate (I)

Step I. [4-(tert-Butyloxycarbonyl)-(3R)-methylpiperazino]-2,6-dichloroquinoline-4-carboxamide (X)

A mixture of 6-chloro-2-hydroxyquinoline-4-carboxylic acid (V, 1.25 g), thionyl chloride (7.0 ml) and DMF (1 drop) is heated at reflux for 1 hr. The resultant mixture is allowed to cool to 20°–25° and was concentrated. Toluene (20 ml) is added and the mixture concentrated. To a mixture of the crude acid chloride, methylene chloride (30 ml), and diisopropylethylamine (1.35 ml) at 0° is added a mixture of tert-butyl (2R)-methyl-1-piperazinecarboxylate (XXIII, PREPARATION 3,1.23 g) and methylene chloride (2.0 ml). The mixture is stirred for 1 hr at 0° and for 16 hrs at 20°–25°. The residue is partitioned between methylene chloride and sodium bicarbonate, the combined organic layers dried over magnesium sulfate, filtered, concentrated, and crystallized from ether/hexane to give [4-(tert-butyloxycarbonyl)-(3R)-methylpiperazino]2,6-dichloroquinoline-4-carboxamide (X), mp 209°–210°; IR (mineral oil) 1689, 1643, 1422, 1287 and 1228 cm$^{-1}$; MS (EI, m/e) 424, 423, 367, 322, 266, 224, 196 and 161.

Step II. tert-Butyl 7-chloro-5-[4-(tert-butyloxycarbonyl)-(3R)-methylpiperazino]imidazo-[1,5-a]quinoline-3-carboxylate (XII)

Potassium tert-butoxide (1.0M in THF, 4.0 ml) is added to a mixture of [4-(tert-butyloxycarbonyl)-(3R)-methylpiperazino]26-dichloroquinoline-4-carboxamide (X, 1.48 g), tert-butyl isocyanoacetate (IX. 615 mg ). THF (14 ml) and DMF (1.0 ml) at −78°. The mixture is stirred for 1 hr at −78° and is allowed to warm to 20°–25° over several hours. After stirring at 20°–25° for 16 hrs, the residue is partitioned between water and methylene chloride, the combined organic phase dried over magnesium sulfate, filtered and concentrated. The concentrate is crystallized from hot ethyl acetate/methanol to provide tert-butyl 7-chloro-5-[4-(tert-butyloxycarbonyl)-(3R)-methylpiperazino]imidazo[1,5-a]-quinoline-3-carboxylate (XII) (mp 246°–247°). Purification of the filtrate by flash chromatography (silica gel; ethyl acetate/hexane (1/1)) gives additional product, IR (mineral oil) 1686, 1646, 1419, 1412, 1389, 1365, 1157 and 1138 cm$^{-1}$; MS (EI, m/e) 529, 528, 399, 371, 273 and 229.

Step III. tert-Butyl 7-chloro-5-[((3R)-methylpiperazino)carbonyl]imidazo[1,5a]quinoline-3-carboxylate (I)

Trifluoroacetic acid (15 ml) is added to a mixture of tert-butyl 7-chloro-5-[4-(tert-butyloxycarbonyl)-(3R)-methylpiperazino]imidazo[1,5-a]quinoline-3-carboxylate (XII, 1.33 g) and methylene chloride (20 ml) at 0°. The mixture is stirred for 1 hr at 0° and is concentrated. The residue is partitioned between methylene chloride and sodium bicarbonate, the combined organic phase dried over magnesium sulfate, filtered, and concentrated. The concentrate is crystallized from ethyl acetate/hexane to provide the title compound, mp 166° dec; [α]$^{25}_D$+11° (CHCl$_3$); IR (mineral oil) 1684, 1645, 1443, 1420, 1392, 1304, 1273, 1246, 1159, 1138 and 1060 cm$^{-1}$; NMR (CDCl$_3$) 8.64, 7.95–8.15, 7.6–7.9, 4.65–4.85, 2.6–3.65, 1.68, 1.23 and 0.9–1.05 δ; MS (EI, m/e) 428, 371, 355, 327, 315, 273 and 229.

Example 20 tert-Butyl 7-chloro-5-[((3S)-methylpiperazino)carbonyl]imidazo[1,5-a]quinoline-3-carboxylate (I)

Following the general procedure of EXAMPLE 19 and making non-critical variations but starting with tert-butyl (2S)-methyl-1-piperazinecarboxylate (XXIII, PREPARATION 3) and 6-chloro-2-hydroxyquinoline-4-carboxylic acid (V, EXAMPLE 15, Step II) the title compound is obtained, mp 163°14 168°; [α]$^{25}_D$−11° (CHCl$_3$).

Example 21 tert-Butyl 7-chloro-5-[(trans-(3S),(5S)-dimethylpiperazino)carbonyl]imidazo[1,5-a]quinoline-3-carboxylate (I)

Step I. [1-[(2S)-[N-[(1,1-dimethylethoxy)carbonyl]]propylamino]-1-((2R)-propanol)amino]2,6-dichloroquinoline-4-carboxamide (XIII)

A mixture of 6-chloro-2-hydroxyquinoline-4-carboxylic acid (V, 1.57 g), thionyl chloride (9.0 ml) and DMF (1 drop) is heated at reflux for 1 hr. The resultant mixture is allowed to cool to 20°–25° and is concentrated. Toluene (25 ml) is added and the mixture concentrated. To a mixture of the crude acid chloride, methylene chloride (30 ml), and diisopropylethylamine (1.65 ml) at 0° is added the amino alcohol (XIV, PREPARATION 1, 1.73 g). The mixture is stirred for 1 hr at 0° and for 16 hrs at 20°–25°. The residue is partitioned between methylene chloride and sodium bicarbonate, the combined organic phase is dried over magnesium sulfate, filtered, concentrated and purified by flash chromatography (silica gel; hexane/ethyl acetate (1/1)) to give the carbamate (XIII) which was carried on crude, mp 81° dec; IR (mineral oil) 1710, 1693, 1627, 1555, 1367, 1247, 1166 and 885 cm$^{-1}$; MS (EI, m/e) 455, 312, 255, 196, 113 and 88.

Step II. [1-[(2S)-propylamino]-1-((2R)-propanol)amino]-2,6-dichloroquinoline-4-carboxamide (XV)

A mixture of the carbamate (XIII,Step I, 1.82 g), methylene chloride (20 ml), and TFA (20 ml) is stirred at 0° for 1 hr and is concentrated. The residue is partitioned between methylene chloride and sodium bicarbonate, the combined organic phase is dried over magnesium sulfate, filtered and concentrated to give the amino alcohol (XV), mp 75°–80° dec; IR (mineral oil) 1633, 1555, 1377, 1080 and 884 cm$^{-1}$; MS (EI, m/e) 356, 355, 338, 312, 292, 225, 197, 88 and 70.

Step III. trans-(3S),(5S)-Dimethylpiperazino 2,6-dichloroquinoline-4-carboxamide (X)

Diethyl azodicarboxylate (DEAD, 0.71 ml) is added to a mixture of the crude amino alcohol (XV, Step II, 1.26 g), triphenylphosphine (1.24 g), and THF (31 ml). The mixture is stirred at 20°–25° for 16 hrs and is concentrated. The concentrate is purified by flash chromatography (silica gel: ethyl acetate/methanol (4/1)) to gives trans-(3S),(5S)-dimethylpiperazino 2,6-dichloroquinoline-4-carboxamide (X) which is carried on crude, IR (mineral oil) 1629, 1433 and 885 cm$^{-1}$; NMR (CDCl$_3$) 8.01, 7.65–7.85, 7.32, 3.85–4.1, 3.05–3.7, 2.89, 1.45–1.85, 1.15–1.35, 1.06 and 0.94;MS (EI, m/e) 338, 337, 293, 224, 196 and 113.

Step IV. tert-Butyl 7-chloro-5-[(trans-(3S),(5S)-dimethylpiperazino)carbonyl]imidazo-[1,5-a]quinoline-3-carboxylate (I)

Potassium tert-butoxide (1.0M in THF, 1.95 ml) is added to a mixture of trans-(3S),(5S)-dimethylpiperazino 2,6-dichloroquinoline-4-carb3 oxamide (X, Step III, 441 mg ), tertbutyl isocyanoacetate (IX, 0.29 ml), and THF (7.0 ml) at 0°. The mixture is stirred for 1 hr at 0° and is allowed to warm to 20°–25° over several hours. After stirring at 20°–25° for 16 hrs, residue is partitioned between water and ethyl acetate, the combined organic phase is dried over magnesium sulfate, filtered, concentrated, and purified by flash chromatography (silica gel; methylene chloride/methanol (20/1)) to give the desired product. Recrystallization from hot ethyl acetate/methanol/hexane/ether gives the title compound, mp 171°–174°; [α]$^{25}_D$−16° (CHCl$_3$); IR (mineral oil) 1685, 1642, 1421, 1390, 1159 and 1137 cm$^{-1}$; NMR (300 MHz, CDCl$_3$) 8.63, 7.95–8.15, 7.7–7.85, 7.67, 3.9–4.1, 3.3–3.65, 3.0–3.3, 1.67, 1.2–1.35 and 0.9–1.2 δ; MS (EI, m/e) 442, 341,273, 229 and 113.

Example 22 tert-Butyl 7-chloro-5-[(trans-(3R),(5R)-dimethylpiperazino)carbonyl]-imidazo[1.5-a]quinoline-3-carboxylate (I)

Following the general procedure of EXAMPLE 21 (S,S-enantiomer) and making non-critical variations but starting with 1-[(2R)-[N-[(1,1-dimethylethoxy)carbonyl]]propylamino]-amino-(2S)-propanol (XIV, PREPARATION 2) and 6-chloro-2-hydroxyquinoline-4-carboxylic acid (V, EXAMPLE 15, Step II) the title compound (the R,R-enantiomer) is obtained, mp 175°–180°; [α]$^{25}_D$+16° (CHCl$_3$).

Example 23 tert-Butyl 7-methyl-5-[(cis-3,5-dimethylpiperazino)carbonyl]imidazo[1,5-a]quinoline-3-carboxylate (I)

Step I. 5-Methylisatin acetamide (IV)

Solid 4-dimethylaminopyridine (151 mg ) is added to a stirred mixture of 5-methylisatin (III, 5.00 g), acetic anhydride (3.2 ml) and THF (44 ml) at 20°–25°. The resulting mixture is stirred for 75 min. The mixture is concentrated, 50 ml of methylene chloride is added, and the mixture is again concentrated. The solids are triturated for 30 min in methylene chloride/hexane (3/1, 100 ml), filtered, washed with methylene chloride/hexane (3/1) and dried to give 5-methylisatin acetamide (IV), mp 171°–172°; IR (mineral oil) 1770, 1738, 1720, 1586, 1487, 1308, 1269 and 1164 cm$^{-1}$; NMR (D$_6$DMSO) 8.15, 7.55–7.6. 2.58 and 2.35 δ; MS (EI, m/e) 203, 160, 133, 104, 77 and 43.

Step II. 2-Hydroxy-6-methylquinoline-4-carboxylic acid (V)

A mixture of 5-methylisatin acetamide (IV, Step I, 2.00 g), potassium hydroxide (1N, 25 ml) and THF (8 ml) is heated at reflux for 75 min, allowing the THF to boil off. The mixture is allowed to cool to 20°–25° and is washed with methylene chloride (2×30 ml) followed by ethyl acetate (2×30 ml). The basic layer is acidified to pH 5.5 (pH paper) with hydrochloric acid (4N). The resulting solids are filtered, washed with water, hexane and dried to give 2-hydroxy-6-methylquinoline-4-carboxylic acid (V), mp >300°; IR (mineral oil) 3001, 1714, 1645, 1520, 1538, 1435, 1217 and 887 cm$^{-1}$; NMR (D$_6$DMSO) 12.02, 7.93, 7.40, 7.28, 6.84 and 2.36 δ; MS (EI, m/e) 203, 158, 130, 103, 77 and 44.

Step III. cis-3,5-Dimethylpiperazino-2-chloro-6-methylquinoline-4-carboxamide (X)

A mixture of 2-hydroxy-6-methylquinoline-4-carboxylic acid (V, Step II, 700 mg ), thionyl chloride (20 ml) and DMF (2 drops) is heated at reflux for 1 hr and is allowed to cool to 20°–25°. Toluene (20 ml) is added and the mixture is concentrated. The concentrate is concentrated twice more from toluene (20 ml). The acid chloride is dissolved in methylene chloride (20 ml) and is added dropwise to a stirred mixture of cis-2,6-dimethylpiperazine (511 mg), diisopropylethylamine (0.90 ml) and methylene chloride (20 ml) at 0°. The mixture is allowed to warm slowly and is stirred overnight at 20°–25°. Water (2 ml) is added and the mixture concentrated. The residue is partitioned between ethyl acetate and sodium bicarbonate, the combined organic phase is dried over magnesium sulfate, filtered, concentrated, and purified by flash chromatography (silica gel; methanol/ethyl acetate (1/9)) to give cis-3,5-dimethylpiperazino 2-chloro-6-methylquinoline-4-carboxamide (X), mp 75°–85°; IR (mineral off) 1639, 1559, 1432, 1318, 1296, 1293 and 1099 cm$^{-1}$; NMR (CDCl$_3$) 7.96, 7.55–7.65, 7.43, 7.2–7.3, 4.7–4.85, 2.4–3.2, 2.53, 1.55, 1.15–1.25, 0.93 and 0.88 δ; MS (EI, m/e) 317, 273, 204, 176, 140, 113, 84 and 70.

Step IV. tert-Butyl 7-methyl-5-[(cis-3.5-dimethylpiperazino)carbonyl]imidazo[1,5-a]quinoline-3-carboxylate (I)

A mixture of cis-3,5-dimethylpiperazino-2-chloro-6-methylquinoline-4-carboxamide (X, Step III. 1.04 g) and THF (15 ml) is cooled to −78°. tert-Butyl isocyanoacetate (IX, 0.58 ml) is added, followed by potassium tert-butoxide (1.0N in THF, 4.0 ml) which is added dropwise over several minutes. The mixture is allowed to warm slowly and is stirred for 3 days at 20°–25°. The mixture is diluted with water (25 ml) and the THF is evaporated under reduced pressure. The solids are filtered, washed with water, dissolved in methanol/ethanol (5/95), dried (magnesium sulfate), filtered, and concentrated to give a solid. Recrystallization from ethyl acetate gives the title compound, mp 244°–245°; IR (mineral oil) 1719, 1708, 1621, 1389, 1269, 1160, 1141 and 1134 cm$^{-1}$; NMR (CDCl$_3$) 8.62, 7.95–8.05, 7.60, 7.51, 7.43, 4.7–4.85, 3.45–3.55, 2.4–3.1, 2.50, 1.68, 1.21, 0.96 and 0.92 δ; MS (EI, m/e) 422, 365, 349, 321, 295, 253, 226, 209, 179, 154, 113, 70 and 42.

EXAMPLE 24 tert-Butyl 4-methyl-5-[(cis-3,5-dimethylpiperazino)carbonyl]-imidazo[1,5-a]quinoline-3-carboxylate (I)

Step I. cis-3,5-Dimethylpiperazino 2-chloro-3-methylquinoline-4-carboxamide (X)

A mixture of 2-hydroxy-3-methylquinoline-4-carboxylic acid (V, 1.62 g), thionyl chloride (10.0 ml) and DMF (1 drop) is heated at reflux for 1 hr. The resultant mixture is allowed to cool to 20°–25° and is concentrated. Toluene (35 ml) is added and the mixture concentrated. To a mixture of the crude acid chloride, methylene chloride (40 ml), and diisopropylethylamine (1.90 ml) at 0° is added cis-2,6-dimethylpiperazine (1.19 g). The mixture is stirred for 1 hr at 0° and for 16 hrs at 20°–25°. The residue is partitioned between methylene chloride and sodium bicarbonate, the combined organic phase is dried over magnesium sulfate, filtered, concentrated, triturated with ethyl acetate/hexane, and filtered to give cis-3,5-dimethylpiperazino 2-chloro-3-methylquinoline-4-carboxamide (X), mp 198°–200°; IR (mineral oil) 1628, 1440, 1321, 1275 and 769 cm$^{-1}$; NMR (CDCl$_3$) 8.03, 7.65–7.8, 7.5–7.65, 4.75–4.9, 2.9–3.1, 2.4–2.9, 2.52, 2.44, 1.3–1.8, 1.15–1.25, 0.92 and 0.85 δ; MS (EI, m/e) 317, 204, 140, 127 and 113.

Step II. tert-Butyl 4-methyl-5-[(cis-3,5-dimethylpiperazino)carbonyl]imidazo[1,5-a]quinoline-3-carboxylate (I)

Potassium tert-butoxide (1.0M in THF, 3.3 ml) is added to a mixture of cis-3,5-dimethylpiperazino-2-chloro-3-methylquinoline-4-carboxamide (X, Step I, 1.00 g), tert-butyl isocyanoacetate (IX, 520 mg) and THF (10.3 ml) at −78°. The mixture is stirred for 1 hr at −78° and is allowed to warm to 20°–25° over several hours. After stirring at 20°–25° for 16 hrs, the residue is partitioned between ethyl acetate and water, the combined organic phase is dried over magnesium sulfate, filtered, concentrated, and purified by flash chromatography (silica gel; ethyl acetate/methanol (4/1)) to give the title compound which is crystallized from ether/hexane, mp 228–232°; NMR (CDCl$_3$) 8.67, 8.05, 7.55–7.7, 7.4–7.55, 4.87, 3.25–3.4, 2.95–3.1, 2.45 2.64, 1.68, 1.22 and 0.89 δ; MS (EI, m/e) 422, 351,307, 227, 209, 113 and 70.

Example 25 tert-Butyl 7-fluoro-4-methyl-5-[(cis-3,5-dimethylpiperazino)carbonyl]imidazo[1,5-a]quinoline-3-carboxylate (I)

Step I. 5—Fluoroisatin propionamide (IV)

A mixture of 5-fluoroisatin (III, 10.4 g), propionic anhydride (12.0 ml), THF (20 ml) and DMAP (20 mg) is heated at reflux for 6 hrs and is allowed to cool to 20°–25°. The mixture is concentrated, triturated with ether/hexane (1/1), filtered and dried to provide 5-fluoroisatin propionamide (IV), mp 142°–145°; IR (mineral oil) 1781, 1752, 1711, 1708, 1482, 1290, 1133 and 850 cm$^{-1}$; NMR (CDCl$_3$)

8.45–8.55, 7.4–7.5, 3.14 and 1.27 δ; MS (EI, m/e) 221, 164, 108 and 57.

Step II. 6—Fluoro-2-hydroxy-3-methylquinoline-4-carboxylic acid (V)

A mixture or 5-fluoroisatin propionamide (IV, Step I, 8.25 g) and potassium hydroxide (1N, 108 ml) is heated at reflux for 6.5 hrs and is allowed to cool to 20°–25°. The mixture is extracted with ethyl acetate (150 ml) to remove 5-fluoroisatin (III). The basic layer is acidified (concentrated hydrochloric acid) to pH 3 and the mixture cooled in an ice bath for 1 hr. The solids are filtered, washed (20 ml) and dried to provide 6-fluoro-2-hydroxy-3-methylquinoline-4-carboxylic acid (V), mp >305°; IR (mineral oil) 1681, 1506, 1263 and 1192 cm$^{-1}$; NMR (d$_6$-DMSO) 12.10, 7.3–7.5, 7.15 and 2.09 δ; MS (EI, m/e) 221,177 and 148.

Step III. cis-3,5-Dimethylpiperazino 2-chloro-6-fluoro-3-methylquinoline-4-carboxamide (x)

A mixture of 6-fluoro-2-hydroxy-3-methyl-4-quinoline carboxylic acid (V, 2.50 g), thionyl chloride (17.0 ml) and DMF (2 drops) is heated at reflux for 2 hrs. The resultant mixture is allowed to cool to 20°–25° and is concentrated. Toluene (25 ml) is added and the mixture concentrated. To a mixture of the crude acid chloride, methylene chloride (50 ml) and diisopropylethylamine (2.70 ml) at 0° is added cis-2,6-dimethylpiperazine (1.55 g). The mixture is stirred for 1 hr at 0° and for 16 hrs at 20°–25°. The residue is partitioned between methylene chloride and sodium bicarbonate, the combined organic phase is dried over magnesium sulfate, filtered, concentrated and purified by flash chromatography (silica gel; ethyl acetate/methanol (4/1)) to give cis-3,5-dimethylpiperazino 2-chloro-6-fluoro-3-methylquinoline-4-carboxamide (X) which is carried on crude, mp 189°–191°; IR (mineral oil) 1629, 1315, 1213, 1029 and 825 cm$^{-1}$; NMR (CDCl$_3$) 8.03, 7.45–7.55, 7.34, 7.18, 4.75–4.9, 2.9–3.1, 2.4–2.9, 2.52, 2.44, 1.4–1.8, 1.22, 1.21, 0.93 and 0.87 δ; MS (EI, m/e) 335, 320, 291,277. 222, 158, 127, 113 and 70.

Step IV. tert-Butyl 7-fluoro-4-methyl-5-[(cis-3,5-dimethylpiperazino)carbonyl]imidazo[1,5-a]quinoline 3-carboxylate (I)

Potassium tert-butoxide (1.0M in THF, 4.5 ml) is added to a mixture of cis-3,5-dimethylpiperazino 2-chloro-6-fluoro-3-methylquinoline-4-carboxamide (X, 1.00 g), tert-butyl isocyanoacetate (IX, 0.67 ml) and THF (16 ml) at 0°. The mixture is stirred for 2 hrs at 0° and 16 hrs at 20°–25°. The mixture is then cooled to 0° and additional isocyanide (IX, 0.67 ml) and potassium tert-butoxide (4.50 ml) are added. The mixture is stirred for 1 hr at 0° and 16 hrs at 20°–25°. The residue is partitioned between ethyl acetate and water, the combined organic layers phase is dried over magnesium sulfate, filtered, concentrated and purified by flash chromatography (silica gel; methylene chloride/methanol (20/1)) to give the title compound which is recrystallized from hot ethyl acetate/methanol/hexane, mp 254°–256°; IR (mineral oil) 1717, 1628, 1479, 1280, 1255 and 1156 cm$^{-1}$; NMR (CDCl$_3$) 8.62, 8.02, 7.25–7.4, 7.13, 4.83, 3.25–3.4, 2.9–3.1, 2.45–2.85, 2.73, 2.64, 1.67, 1.22, 1.15–1.3, 0.95 and 0.90 δ; MS (EI, m/e) 440, 369, 325, 253 and 70.

Example 26 tert-Butyl 7-chloro-4-methyl-5-[(cis-3,5-dimethylpiperazino)carbonyl]imidazo[1,5-a]quinoline-3-carboxylate (I)

Step I. 5-Chloroisatin propionamide (IV)

A mixture of 5-chloroisatin (III, 10.0 g), propionic anhydride (10.0 ml), THF (20 ml) and DMAP (20 mg) is heated at reflux for 16 hrs and is allowed to cool to 20°–25°. The mixture is concentrated, triturated with ether/hexane (1/1), filtered and dried to provide 5-chloroisatin propionamide (IV), mp 112° dec; IR (mineral oil) 1790, 1743, 1737, 1706, 1301, 1286, 1167 and 1137 cm$^{-1}$; NMR (CDCl$_3$) 8.44, 7.75, 7.68, 3.14 and 1.27 δ; MS (EI, m/e) 237, 180 and 124.

Step II. 6-Chloro-2-hydroxy-3-methylquinoline-4-carboxylic acid (V)

A mixture of 5-chloroisatin propionamide (IV, Step I, 8.89 g) and potassium hydroxide (1N, 120 ml) is heated at reflux for 6.5 hrs and is allowed to cool to 20°–25°. The mixture is extracted several times with ethyl acetate to remove 5-chloroisatin. The basic layer is acidified (10% hydrochloric acid) to pH 3 and the mixture cooled in an ice bath for 1 hr. The resulting solids are filtered, washed (20 ml) and dried to provide 6-chloro-2-hydroxy-3-methylquinoline-4-carboxylic acid (V), mp 278° dec; IR (mineral oil) 1709, 1678 and 1620 cm$^{-1}$; NMR (D$_6$DMSO) 12.15, 7.57, 7.3–7.45, 3.38 and 2.09 δ; MS (EI, m/e) 237, 207, 193, 181, 164, 153 and 126.

Step III. cis-3,5-Dimethylpiperazino 2,6-dichloro-3-methylquinoline-4-carboxamide (X)

A mixture of 6-chloro-2-hydroxy-3-methylquinoline-4-carboxylic acid (V, Step II, 1.44 g), thionyl chloride (9.0 ml) and DMF (1 drop) is heated at reflux for 2 hrs. The resultant mixture is allowed to cool to 20°–25° and was concentrated. Toluene (25 ml) is added and the mixture concentrated. To a mixture of the crude acid chloride, methylene chloride (30 ml), and diisopropylethylamine (1.46 ml) at 0° is added cis-2,6-dimethylpiperazine (831 mg). The mixture is stirred for 1 hr at 0° and for 16 hrs at 20°–25°. The residue is partitioned between methylene chloride and sodium bicarbonate, the combined organic phase is dried over magnesium sulfate, filtered, concentrated and purified by flash chromatography (silica gel; ethyl acetate/methanol (6/1)) to give cis-3,5-dimethylpiperazino 2,6-dichloro-3-methylquinoline-4-carboxamide (X), mp 177°–180°; IR (mineral oil) 1635, 1317, 1268 and 1002 cm$^{-1}$; NMR (CDCl$_3$) 7.97, 7.6–7.75, 7.53, 4.83, 2.4–3.1, 2.51, 2.43, 1.4–1.7, 1.22, 1.21, 0.94 and 0.88 δ; MS (EI, m/e) 352, 351, 307, 238, 127 and 113.

Step IV. tert-Butyl 7-chloro-4-methyl-5-[(cis-3,5-dimethylpiperazino)carbonyl]imidazo[-1,5-a]quinoline-3-carboxylate (I)

Potassium tert-butoxide (1.0M in THF, 3.9 ml) is added to a mixture of cis-3,5-dimethylpiperazino 2,6-dichloro-3-methylquinoline-4-carboxamide (X, 911 mg), tert-butyl isocyanoacetate (IX, 0.58 ml), and THF (14 ml) at 0°. The mixture is stirred for 1 hr at 0° and is allowed to warm to 20°–25° over several hours. After stirring at 20°–25° for 16 hrs, the mixture is cooled to 0° and additional isocyanide (IX, 0.58 ml) and tert-butoxide (3.9 ml) are added. The mixture is allowed to gradually warm to 20°–25° and is stirred for an additional 3 days. The residue is partitioned between water and methylene chloride, the combined organic phase is dried over magnesium sulfate, filtered, concentrated and purified by flash chromatography (silica gel; methylene chloride/methanol (20/1)) to give the product. Recrystallization from hot ethyl acetate/methanol/hexane gives the rifle compound, mp 264°–267°; IR (mineral oil) 1716, 1626, 1479, 1462, 1160 and 1142 cm$^{-1}$; NMR (CDCl$_3$) 8.63, 7.98, 7.55–7.65, 7.42, 4.85, 3.2–3.35, 2.8–3.1, 2.45–2.8, 2.73, 2.63, 1.67, 1.22, 1.21, 0.95 and 0.90 δ; MS (EI, m/e) 456, 385, 341, 269, 243, 127, 113 and 70.

Example 27

Pyrrolidino 3-(5-cyclopropyl-1,2,4-oxadiazol-3-yl)-7-chloroimidazo[1,5-a]quinoline-5-carboxamide (I)

Following the general procedure of EXAMPLE 12 and making non-critical variations but using 5-cloroisatin (III) in Step I, and using pyrrolidine in place of morpholine in Step II, the title compound is obtained, NMR (CDCl$_3$) 8.72, 8.12, 8.01, 7.84, 7.63, 3.79, 3.39, 2.30, 2.06, 1.95, 1.40 and 1.28 δ.

Example 28 tert-Butyl 7-chloro-5-[((3R),5,5-trimethylpiperazino)carbonyl]imidazo-[1,5-a]quinoline-3-carboxylate (I)

Step I. [(4-tert-Butyloxycarbonyl)-(3R),5,5-trimethylpiperazino]-2,6-dichloroquinoline-4-carboxamide (X)

A mixture of (2R),6,6-trimethylpiperazine dihydrochloride (XXXI, 258 mg) and methylene chloride (5 ml) is stirred at 0° and diisopropylethylamine (0.74 ml) is added. The mixture is stirred at 0° for 15 min and at 20°–25° for 30 min. The mixture is cooled to 0° and the acid chloride (VB, prepared as in EXAMPLE 15, Step III, 318 mg) is added. The mixture is allowed to warm slowly and stir at 20°–25° for 12–24 hr. Basic workup (ethyl acetate, sodium bicarbonate and magnesium sulfate) and purification by flash chromatography (methanol/ethyl acetate 10/90) gives the title compound as a solid (X), mp 86°–87°; IR (mineral oil) 1636, 1629, 1555, 1432, 1295 and 885 cm$^{-1}$; MS (EI, m/e) 351,293, 196, 161, 141, 127 and 84.

Step II. tert-Butyl 7-chloro-5-[((3R),5,5-trimethylpiperazino)carbonyl]imidazo[1,5a]quinoline-3-carboxylate (I)

A solution of the amide (X, 369 mg), tert-butyl isocyanoacetate (IX, 0.18 mL) and THF (4 ml) is cooled to 0°. Potassium tert-butoxide (1.0M in THF, 1.3 ml) is added and the mixture is allowed to warm and is stirred at 20°–25° for 4 hr. Basic workup (ethylacetate, sodium bicarbonate and magnesium sulfate), flash chromatography (methanol/ethyl acetate, 10/90) and crystallization from ethyl acetate/hexane gives the title compound (I) as a solid, mp 225°–226°; [α]$^{25}_D$ –3° (chloroform); IR (mineral oil) 1719, 1627, 1616, 1388, 1154, and 1134, cm$^{-1}$; MS (EI, m/e) 456, 399, 383, 355, 273, 229, 174, 141, 127 and 84.

Example 29 tert-Butyl 7-chloro-5-[((3S),5,5-trimethylpiperazino)carbonyl]imidazo-]1,5-a]quinoline- 3-carboxylate (I)

Following the general procedure of EXAMPLE 28 and making non-critical variations but starting with (2S),6,6-trimethylpiperazine (XXXI) dihydrochloride and 6-chloro-2-hydroxyquinoline-4-carboxylic acid (V, EXAMPLE 15, Step II) the title compound is obtained, mp 225°–226°; [α]$^{25}_D$+3° (chloroform).

CHART A

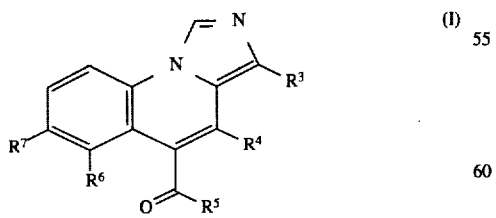

CHART B

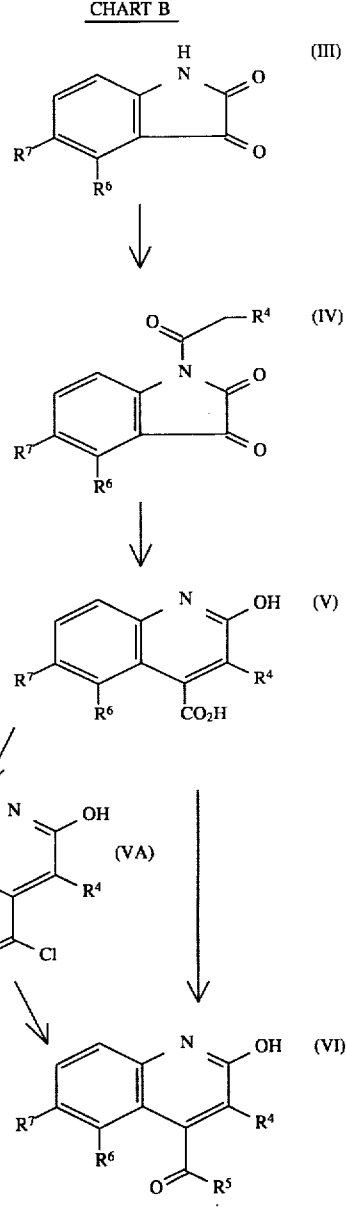

-continued
CHART B
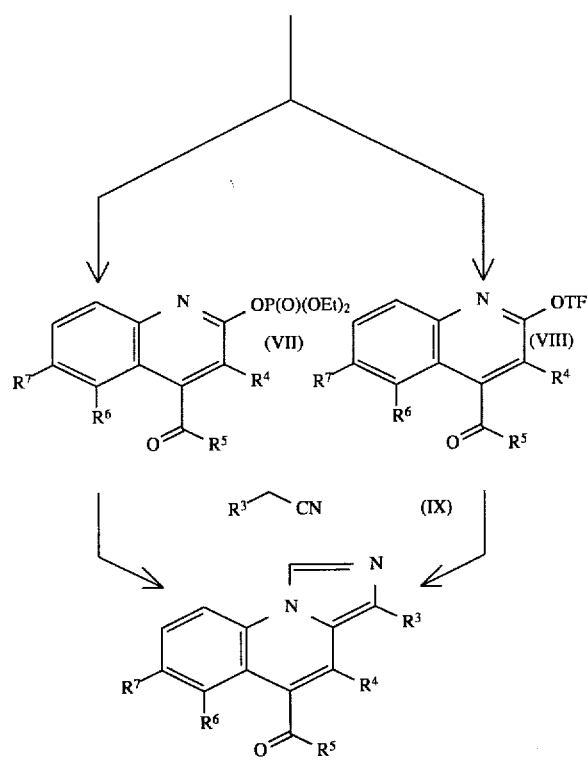
CHART C
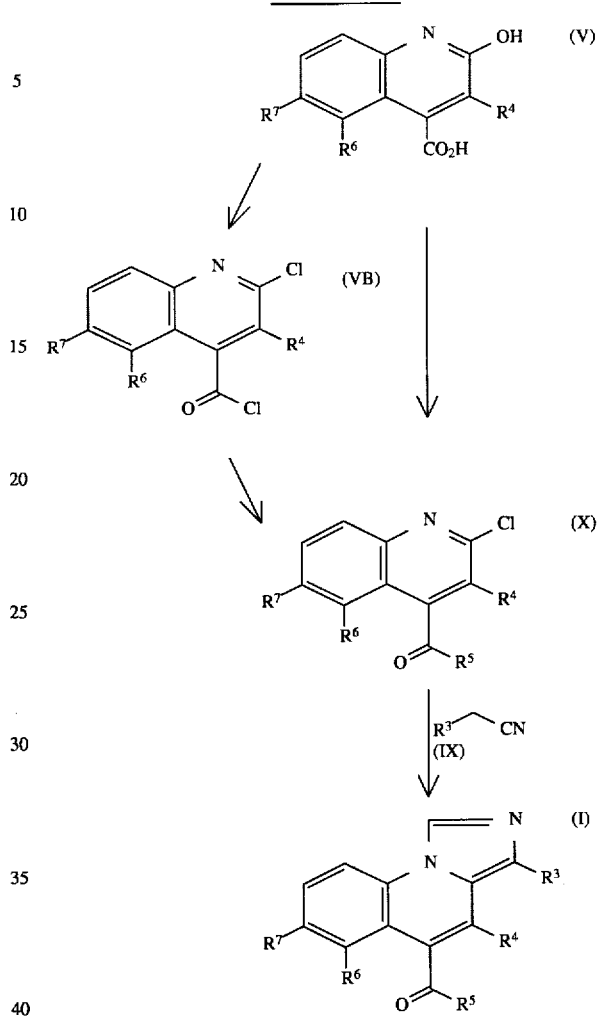
CHART D
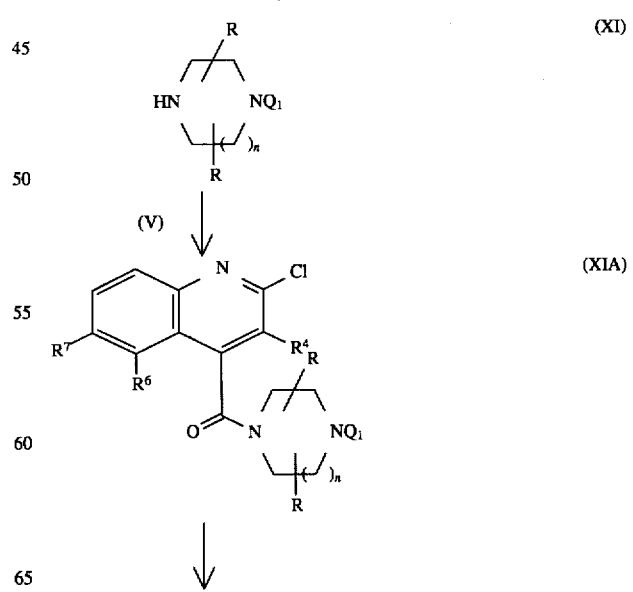

39
-continued
CHART D
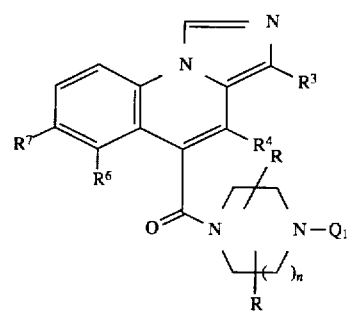
(XII)
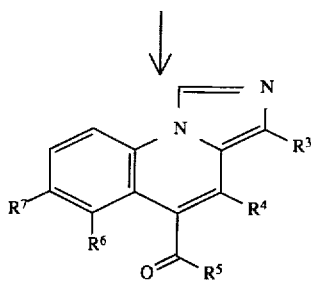
(I)
CHART E
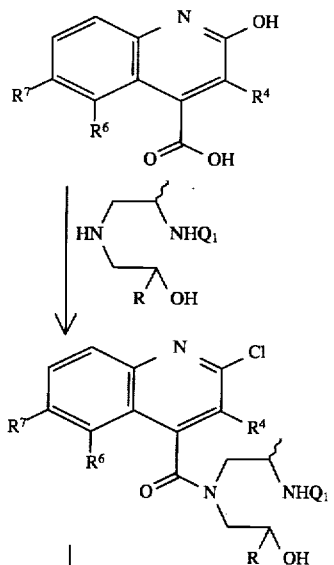
(V)
(XIV)
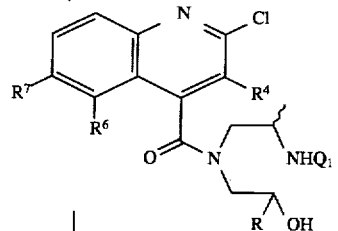
(XIII)
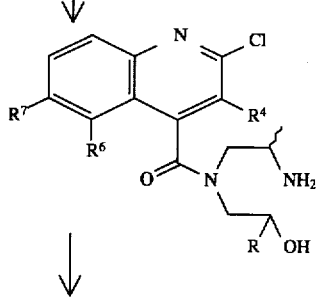
(XV)
40
-continued
CHART E
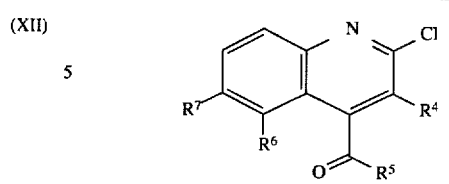
(X)
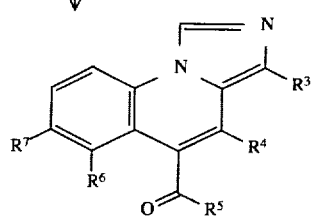
(I)
CHART F
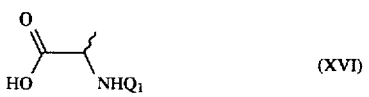
(XVI)
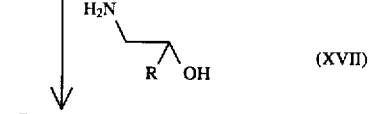
(XVII)
(XVIII)
(XIV)
CHART G
(XVI)
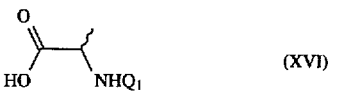

CHART G -continued
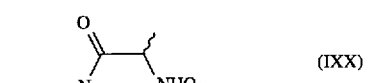
(IXX)
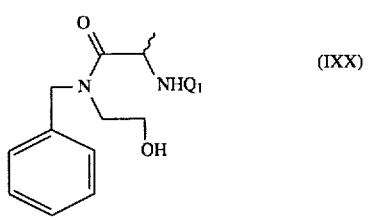
(XX)
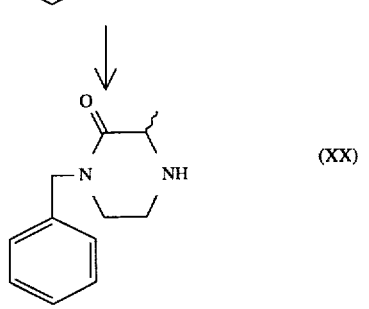
(XXI)
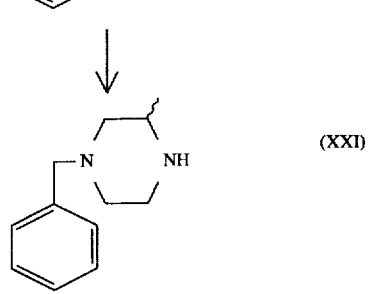
(XXII)
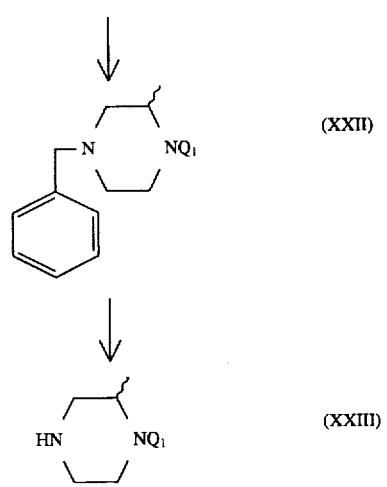
(XXIII)
CHART H
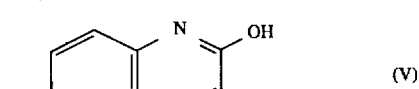
(V)
CHART H -continued
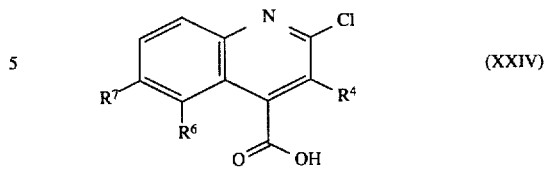
(XXIV)
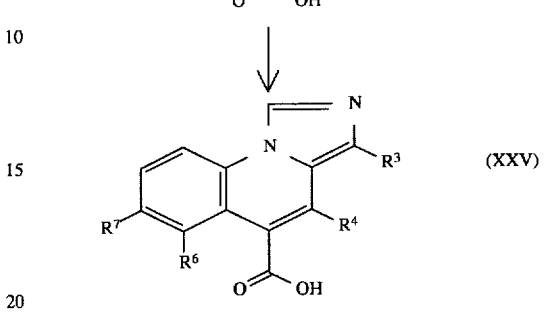
(XXV)
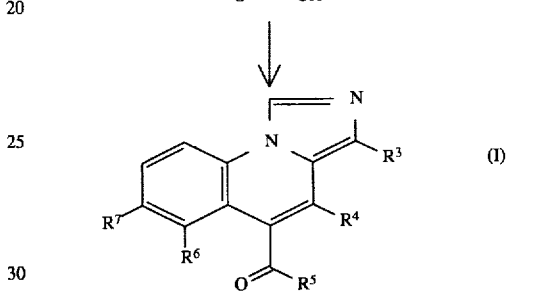
(I)
CHART I
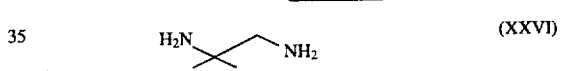
(XXVI)
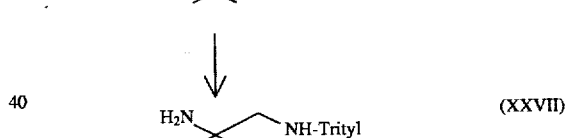
(XXVII)
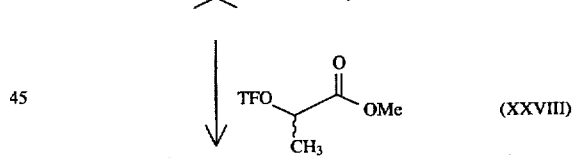
(XXVIII)
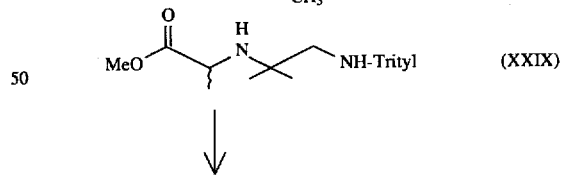
(XXIX)

-continued
CHART I

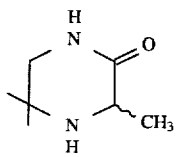

(XXX)

↓

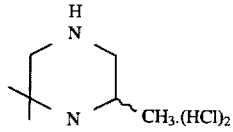

(XXXI)

We claim:
1. Imidazo[1,5-a]quinolines of formula (I)

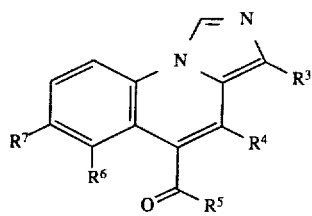

(I)

where
(I) $R_3$ is
   (A) —CO—OR$_{3-1}$ where R$_{3-1}$ is
      (1) —H,
      (2) $C_1$–$C_6$ alkyl,
      (3) $C_3$–$C_7$ cycloalkyl,
      (4) —($C_1$–$C_6$ alkyl)—$C_3$–$C_7$ cycloalkyl,
      (5) —(CH$_2$)$_n$—CF$_3$ where n is 0 thru 4,
      (6) —(CH$_2$)$_n$—CHF$_2$ where n is defined above,
      (7) —(CH$_2$)$_n$—CH$_2$F where n is defined above,
      (8) —φ optionally substituted with one or two
         (a) —F,
         (b) —Cl,
         (c) —Br,
         (d) —I,
         (e) $C_1$–$C_4$ alkyl,
         (f) —NR$_{3-2}$R$_{3-3}$ where R$_{3-2}$ and R$_{3-3}$ are the same or different and are selected from the group consisting of
            (i) —H,
            (ii) $C_1$–$C_6$ alkyl,
            (iii) $C_3$–$C_7$ cycloalkyl,
            (iv) —($C_{1-C4}$ alkyl)—$C_3$–$C_7$ cycloalkyl, and where R$_{3-2}$ and R$_{3-3}$ are taken together with the attached nitrogen atom to form a heterocyclic moiety selected from the group consisting of pyrrolidinyl, morpholinyl, piperazinyl and piperidinyl,
   (B) —CO—R$_{3-5}$ where R$_{3-5}$ is
      (1) —H,
      (2) $C_1$–$C_6$ alkyl,
      (3) —φ optionally substituted with one or two
         (a) —F,
         (b) —Cl,
         (c) —Br,
         (d) —I,
         (e) $C_1$–$C_4$ alkyl,
         (f) —NR$_{3-2}$R$_{3-3}$ where R$_{3-2}$ and R$_{3-3}$ are defined above, (C) aryl where aryl is
      (1) phenyl

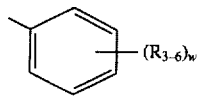

where w is 1 or 2 and where R$_{3-6}$ is
         (a) —H,
         (b) —F,
         (c) —Cl,
         (d) —Br,
         (e) —I,
         (f) —CN,
         (g) —NO$_2$,
         (h) —O—CO—R$_{3-1}$ where R$_{3-1}$ is defined above,
         (i) —(CH$_2$)$_n$—CF$_3$ where n is defined above,
         (j) $C_1$–$C_6$ alkyl,
         (k) $C_3$–$C_7$ cycloalkyl,
         (l) —($C_1$–$C_4$ alkyl)—$C_3$–$C_7$ cycloalkyl,
         (m) —NR$_{3-2}$R$_{3-3}$ where R$_{3-2}$ and R$_{3-3}$ are defined above,
         (n) —(CH$_2$)$_n$—O—R$_{3-1}$ where R$_{3-1}$ and n are defined above,
         (o) —(CH$_2$)$_n$—S—R$_{3-1}$ where R$_{3-1}$ and n are defined above,
         (P) —(CH$_2$)$_n$—CO—O—R$_{3-1}$ where R$_{3-1}$ and n are defined above,
         (q) —N$_{3-1}$—CO—R$_{3-1}$ where the R$_{3-1}$ 's are the same or different and are defined above,
         (r) —SO$_2$—NR$_{3-2}$R$_{3-3}$ where R$_{3-2}$ and R$_{3-3}$ are defined above,
         (s) —CO—R$_{3-5}$ where R$_{3-5}$ is defined above,
         (t) —NH—SO$_2$—CH$_3$,
         (u) —CO—N(R$_{3-4}$)$_2$ where the R$_{3-4}$ may be the same or different and are —H or $C_1$–$C_3$) alkyl,
      (2) 5-substituted-1,2,4-oxadiazol-3-yl

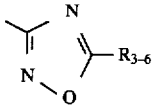

where R$_{3-6}$ is defined above,
      (3) 3-substituted-1,2,4-oxadiazol-5-yl

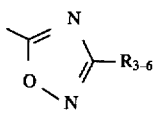

where R$_{3-6}$ is as defined above,
      (4) 4- or 5-substituted isoxazol-3-yl

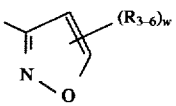

where w and R$_{3-6}$ are defined above, (5) 3- or 4-substituted isoxazol-5-yl

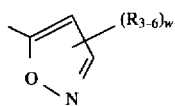

where w and $R_{3-6}$ are defined above;
(II) $R_4$ is
  (A) —H,
  (B) $C_1$-$C_4$ alkyl,
  (C) —$CF_3$;
(III) $R_5$ is
  (A) $C_1$-$C_6$ alkyl,
  (B) —φ optionally substituted with 1 or 2
    (1) —F,
    (2) —Cl,
    (3) —Br,
    (4) —I,
    (5) —CN,
    (6) —$NO_2$,
    (7) —O—CO—$R_{5-1}$ where $R_{5-1}$ is
      (a) —H,
      (b) $C_1$-$C_6$ alkyl,
      (c) $C_3$-$C_7$ cycloalkyl,
      (d) —($C_1$-$C_6$ alkyl)—$C_3$-$C_7$ cycloalkyl,
      (e) —$(CH_2)_b$—$CF_3$ where b is 0 thru 4,
      (f) —$(CH_2)_b$—$CHF_2$ where b is defined above,
      (g) —$(CH_2)_b$—$CH_2F$ where b is defined above,
    (8) —$(CH_2)_b$—$CF_3$ where b is defined above,
    (9) $C_1$-$C_6$ alkyl,
    (10) $C_3$-$C_7$ cycloalky,
    (11) —($C_1$-$C_4$ alkyl)—$C_3$-$C_7$ cycloalkyl,
    (12) —$NR_{5-2}$ where $R_{5-2}$ and $R_{5-3}$ are the same or different and are defined above,
    (13) —$(CH_2)_b$—O—$R_{5-1}$ where $R_{5-1}$ and b are defined above,
    (14) —$(CH_2)_b$—S—$R_{5-1}$ where $R_{5-1}$ and b are defined above,
    (15) —$(CH_2)_b$—CO—O—$R_{5-1}$ where $R_{5-1}$ and b are defined above,
    (16) —$NR_{5-1}$ 13 CO—$R_{5-1}$ where the $R_{5-1}$'s are the same or different and are defined above,
    (17) —$SO_2$—$NR_{5-2}R_{5-3}$ where $R_{5-2}$ and $R_{5-3}$ are defined above,
    (18) —CO—$R_{5-4}$ where $R_{5-4}$ is
      (a) —H,
      (b) $C_1$-$C_6$ alkyl,
      (c) —$N(R_{5-1})_2$ where the $R_{5-1}$s are the same or different and are as defined above,
  (C) —O—$R_{5-5}$ where $R_{5-5}$ is
    (1) —H,
    (2) $C_1$-$C_6$ alkyl,
    (3) $C_3$-$C_7$ cycloalkyl,
    (4) —($C_1$-$C_6$ alkyl)—$C_3$-$C_7$ cycloalkyl,
    (5) —$(CH_2)_b$—$CF_3$ where b is defined above,
    (6) —$(CH_2)_b$—$CHF_2$ where b is defined above,
    (7) —$(CH_2)_b$—$CH_2F$ where b is defined above,
    (8) —φ optionally substituted with one or two
      (a) —F,
      (b) —Cl,
      (c) —Br,
      (d) —I,
      (e) $C_1$-$C_4$ alkyl,
      (f) —$NR_{5-2}R_{5-3}$ where $R_{5-2}$ and $R_{5-3}$ are defined above,
  (D) —$NR_{5-6}R_{5-7}$ where $R_{5-6}$ and $R_{5-7}$ are the same or different and are selected from the group consisting of (1) —H,
(2) $C_1$-$C_6$ alkyl,
(3) $C_3$-$C_7$ cycloalkyl,
(4) —($C_1$-$C_4$ alkyl)—$C_3$-$C_7$ cycloalkyl and where $R_{5-6}$ and $R_{5-7}$ are taken together with the attached nitrogen atom to form a heterocyclic moiety selected from the group consisting of
(a)

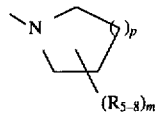

where m is 1 thru 4, p is 0 thru 4 and $R_{5-8}$ is selected from the group consisting of
(i) —H,
(ii) $C_1$-$C_6$ alkyl,
(iii) $C_3$-$C_7$ cycloalkyl,
(iv) —($C_1$-$C_6$ alkyl)—$C_3$-$C_7$ cycloalkyl,
(v) —$(CH_2)_b$—$CF_3$ where b is defined above,
(vi) —$(CH_2)_b$—$CHF_2$ where b is defined above,
(vii) —$(CH_2)_b$—$CH_2F$ where b is defined above,
(viii) —φ optionally substituted with 1 or 2
  (I) —F,
  (II) —Cl,
  (III) —Br,
  (IV) —I,
  (v) $C_1$-$C_4$ alkyl,
  (VI) —$NH_2$,
  (VII) —CO—$NH_2$,
  (VIII) —$SO_2$—$NH_2$,
  (IX) —NH—$SO_2$—$CH_3$,
(b)

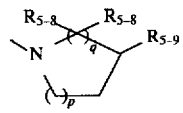

where m and $R_{5-8}$ are defined above,
(c)

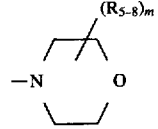

where q is 1 or 2, where p and $R_{5-8}$ are defined above and where $R_{5-9}$ is
(A) —H,
(B) $C_1$-$C_6$ alkyl,
(C) $C_3$-$C_7$ cycloalkyl,
(D) —($C_1$-$C_6$ alkyl)—$C_3$-$C_7$ cycloalkyl,
(E) —$(CH_2)_b$—$CF_3$ where b is defined above,
(F) —$(CH_2)_b$—$CHF_2$ where b is defined above,
(G) —$(CH_2)_b$—$CH_2F$ where b is defined above,
(H) —φ optionally substituted with one or two
  (1) —F,
  (2) —Cl,
  (3) —Br,
  (4) —I,
  (5) $C_1$-$C_4$ alkyl,
  (6) —$NH_2$, (d)

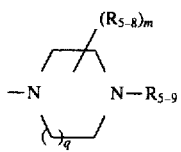

where m, q, $R_{5-8}$ and $R_{5-9}$ are defined above, (e)

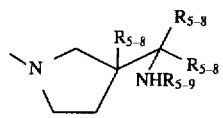

where $R_{5-8}$ and $R_{5-9}$ are defined above, (f)

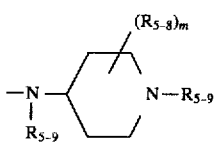

where m, $R_{5-8}$ and $R_{5-9}$ are defined above, (IV) $R_6$ is
- (A) —H,
- (B) —F,
- (C) —Br,
- (D) —I,
- (E) $C_1$–$C_4$ alkyl,
- (F) —CN,
- (G) —NO$_2$,
- (H) —(CH$_2$)$_g$—CF$_3$ where g is 0 thru 4,
- (I) —(CH$_2$)$_g$—OR$_{6-1}$ where $R_{6-1}$ is
  - (1) —H,
  - (2) $C_1$–$C_6$ alkyl
  - (3) —φ optionally substituted with one or two
    - (a) —F,
    - (b) —Cl,
    - (c) —Br,
    - (d) —I,
    - (e) $C_1$–$C_4$ alkyl,
- (f) —NR$_{6-2}$R$_{6-3}$ where $R_{6-2}$ and $R_{6-3}$ are the same or different and are selected from the group consisting of
  - (i) —H,
  - (ii) $C_1$–$C_6$ alkyl,
  - (iii) $C_3$–$C_7$ cycloalkyl,
  - (iv) —($C_1$–$C_4$ alkyl)—$C_3$–$C_7$ cycloalkyl, and where $R_{6-2}$ and $R_{6-3}$ are taken together with the attached nitrogen atom to form a heterocyclic moiety selected from the group consisting of pyrrolidinyl, morpholinyl, piperazinyl, piperdinyl,
- (J) —CO—O—R$_{6-4}$ where $R_{6-4}$ is
  - (1) —H,
  - (2) $C_1$–$C_6$ alkyl,
  - (3) $C_3$–$C_7$ cycloalkyl,
  - (4) —($C_1$–$C_6$ alkyl)—$C_3$–$C_7$ cycloalkyl,
  - (5) —(CH$_2$)$_g$—CF$_3$ where g is defined above,
  - (6) —(CH$_2$)$_g$—CHF$_2$ where g is defined above,
  - (7) —(CH$_2$)$_g$—CH$_2$F where g is defined above,
  - (8) —φ optionally substituted with one or two
    - (a) —F,
    - (b) —Cl,
    - (c) —Br,
    - (d) —I,
    - (e) $C_1$–$C_4$ alkyl,
    - (f) —NR$_{6-2}$R$_{6-3}$ where $R_{6-2}$ and $R_{6-3}$ are as defined above,
- (K) —CO—NR$_{6-2}$R$_{6-3}$ where $R_{6-2}$ and $R_{6-3}$ are as defined above,
- (L) —(CH$_2$)$_g$—NR$_{6-2}$R$_{6-3}$ where g, $R_{6-2}$ and $R_{6-3}$ are defined above,
- (M) —NH—CO—R$_{6-4}$ where $R_{6-4}$ is defined above,
- (N) —SO$_2$—NR$_{6-2}$R$_{6-3}$ where $R_{6-2}$ and $R_{6-3}$ are defined above,
- (O) —N$_3$;

(V) $R_7$ is
- (A) —H,
- (B) —F,
- (C) —Br,
- (D) —I,
- (E) $C_1$–$C_4$ alkyl,
- (F) —CN,
- (G) —NO$_2$,
- (H) —(CH$_2$)$_g$—CF$_3$ where g is 0 thru 4,
- (I) —(CH$_2$)$_g$—OR$_{7-1}$ where $R_{7-1}$ is
  - (1) —H,
  - (2) $C_1$–$C_6$ alkyl,
  - (3) —φ optionally substituted with one or two
    - (a) —F,
    - (b) —Cl,
    - (c) —Br,
    - (d) —I,
    - (e) $C_1$–$C_4$ alkyl,
    - (f) —NR$_{7-2}$R$_{7-3}$ where $R_{7-2}$ and $R_{7-3}$ are the same or different and are selected from the group consisting of
      - (i) —H,
      - (ii) $C_1$–$C_6$ alkyl,
      - (iii) $C_3$–$C_7$ cycloalkyl,
      - (iv) —($C_1$–$C_4$ alkyl)—$C_3$–$C_7$ cycloalkyl, and where $R_{6-2}$ and $R_{7-3}$ are taken together with the attached nitrogen atom to form a heterocyclic moiety selected from the group consisting of pyrrolidinyl, morpholinyl, piperazinyl, piperdinyl,
- (J) —CO—O—R$_{7-4}$ where $R_{7-4}$ is
  - (1) —H,
  - (2) $C_1$–$C_6$ alkyl,
  - (3) $C_3$–$C_7$ cycloalkyl,
  - (4) —($C_1$–$C_6$ alkyl)—$C_3$–$C_7$ cycloalkyl,
  - (5) —(CH$_2$)$_g$—CF$_3$ where g is defined above,
  - (6) —(CH$_2$)$_g$—CHF$_2$ where g is defined above,
  - (7) —(CH$_2$)$_g$—CH$_2$F where g is defined above,
  - (8) —φ optionally substituted with one or two
    - (a) —F,
    - (b) —Cl,
    - (c) —Br,
    - (d) —I,
    - (e) $C_1$–$C_4$ alkyl,
    - (f) —NR$_{7-2}$R$_{7-3}$ where $R_{7-2}$ and $R_{7-3}$ are as defined above,
- (K) —CO—NR$_{7-2}$R$_{7-3}$ where $R_{7-2}$ and $R_{7-3}$ are as defined above,
- (L) —(CH$_2$)$_g$—NR$_{7-2}$R$_{7-3}$ where g, $R_{7-2}$ and $R_{7-3}$ are defined above,
- (M) —NH—CO—R$_{7-4}$ where $R_{7-4}$ is defined above,
- (N) —SO$_2$—NR$_{7-3}$ where $R_{7-2}$ and $R_{7-3}$ are defined above,
- (O) —N$_3$; and pharmaceutically acceptable salts thereof.

2. Imidazo[1,5-a]quinolines (I) according to claim 1 where $R_3$ is (1) 5-substituted-1,2,4-oxadiazol-3-yl

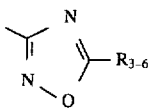

(2) —CO—OR$_{3-1}$.

3. Imidazo[1,5-a]quinolines (I) according to claim 2 where $R_{3-6}$ is $C_3$ cycloalkyl.

4. Imidazo[1,5-a]quinolines (I) according to claim 2 where $R_{3-1}$ is $C_1$–$C_6$ alkyl and where $R_{3-6}$ is $C_3$–$C_7$ cycloalkyl.

5. Imidazo[1,5-a]quinolines (I) according to claim 1 where $R_4$ is —H and $C_1$ alkyl.

6. Imidazo[1,5-a]quinolines (I) according to claim 5 where $R_4$ is —H.

7. Imidazo[,1,5-a]quinolines (I) according to claim 1 where $R_5$ is —NR$_{5-6}$R$_{5-7}$.

8. Imidazo[1,5-a]quinolines (I) according to claim 7 where $R_{5-6}$ and $R_{5-7}$ are cyclized to form a heterocyclic moiety selected from the group consisting of (a)

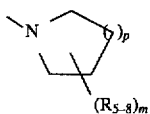

(b)

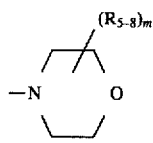

and (d)

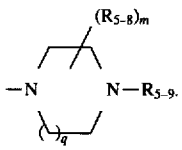

9. Imidazo[1,5-a]quinolines (I) according to claim 8 where q is 1, $R_{5-8}$ is —H or $C_1$ alkyl and where $R_{5-9}$ is —H or $C_1$ alkyl.

10. Imidazo[1,5-a]quinolines (I) according to claim 1 where $R_6$ is —H and —F.

11. Imidazo[1,5-a]quinolines (I) according to claim 10 where $R_6$ is —H.

12. Imidazo[1,5-a]quinolines (I) according to claim 1 where $R_7$ is —H, —F, —Cl —CF$_3$ and $C_1$–$C_4$ alkyl.

13. Imidazo[1,5-a]quinolines (I) according to claim 12 where $R_7$ is —H and —Cl.

14. Imidazo[1,5-a]quinolines (I) according to claim 1 which are selected from the group consisting of pyrrolidino 3-(5-cyclopropyl-1,2,4-oxadiazol-3-yl)imidazo[1,5-a]quinoline-5-carboxamide, dimethylamino 3-(5-cyclopropyl-1,2,4-oxadiazol-3-yl)-imidazo[1,5-a]quinoline-5-carboxamide, tert-butyl 4-[(pyrrolidino)carbonyl]imidazo[1,5-a]quinoline-3-carboxylate, pyrrolidino 3-[5-(1-methylethyl)-1,2,4-oxadiazol-3-yl]imidazo[1,5-a]quinoline-5-carboxamide, pyrrolidino 3-[5-(1,1-dimethylethyl)-1,2,4-oxadiazol-3-yl]imidazo [1,5-a]quinoline-5-carboxamide, pyrrolidino 3-phenylimidazo[1,5-a]quinoline-5-carboxamide, morpholino 3-(5-cyclopropyl-1,2,4-oxadiazol-3-yl)imidazo[1,5-a]quinoline-5-carboxamide, tert-butyl 4-methyl-5-[(pyrrolidino)carbonyl]imidazo[1,5-a]quinoline-3-carboxylate, pyrrolidino 4-methyl-3-[5-(1-methylethyl)-1,2,4-oxadiazol-3-yl]imidazo[1,5-a]quinoline-5-carboxamide, dimethylamino 3-(5-cyclopropyl-1,2,4-oxadiazol-3-yl)-4-methylimidazo[1,5-a]quinoline- 5-carboxamide, pyrrolidino 3-(5-cyclopropyl-1,2,4-oxadiazol-3-yl)-4-methylimidazo[1,5-a]quinoline-5carboxamide, tert-butyl 5-[(cis-3,5-dimethylpiperazino)carbonyl]imidazo[1,5-a]quinoline-3-carboxylate, tert-butyl 7-fluoro-5-[(3,5-dimethylpiperazino)carbonyl]-imidazo[1,5-a]quinoline-3-carboxylate, tert-butyl 7-chloro-5-[(cis-3,5-dimethylpiperazino)carbonyl]imidazo[1,5-a]quinoline-3-carboxylate, tert-butyl 7-chloro-5-[(3,3,5,5-tetramethylpiperazino)carbonyl]imidazo[1,5-a]quinoline-3-carboxylate tert-butyl 7-chloro-5-[(piperazino)carbonyl]imidazo[1,5-a]quinoline-3-carboxylate, tert-butyl 7-chloro-5-[(4-cyclopropylpiperazino)carbonyl]imidazo[1,5-a]quinoline-3-carboxylate, tert-butyl 7-chloro-5-[((3R)-methylpiperazino)carbonyl] imidazo[1,5-a]quinoline-3-carboxylate, tert-butyl 7-chloro-5-[((3S)-methylpiperazino)carbonyl] imidazo[1,5-a]quinoline-3-carboxylate, tert-butyl 7-chloro-5-[(trans-(3S),(5S)-dimethylpiperazino)carbonyl]imidazo[1,5-a]quinoline-3-carboxylate, tert-butyl 7-chloro-5-[(trans-(3R),(5R)-dimethylpiperazino)carbonyl]imidazo[1,5-a]quinoline-3-carboxylate, tert-butyl 7-methyl-5-[(cis-3,5-dimethylpiperazino)carbonyl]imidazo[1,5-a]quinoline-3-carboxylate, tert-butyl 4-methyl-5-[(cis-3,5-dimethylpiperazino)carbonyl]imidazo[1,5-a]quinoline-3-carboxylate, tert-butyl 7-fluoro-4-methyl-5-[(cis-3,5-dimethylpiperazino)carbonyl]imidazo[1,5a]quinoline-3-carboxylate, tert-butyl 7-chloro-4-methyl-5-[(cis-3,5-dimethylpiperazino)carbonyl]imidazo[1,5a]quinoline-3-carboxylate, pyrrolidino 3-(5-cyclopropyl-1,2,4-oxadiazol-3-yl)-7-chloroimidazo[1,5-a]quinoline-5carboxamide, tert-butyl 7-chloro-5-[((3R),5,5-trimethylpiperazino)carbonyl]imidazo[1,5-a]quinoline-3carboxylate, tert-butyl 7-chloro-5-[((3S),5,5-trimethylpiperazino)carbonyl]imidazo[1,5-a]quinoline-3carboxylate.

15. An imidazo[1,5-a]quinoline (I) according to claim 14 which is tert-butyl 7-chloro-5-[(cis-3,5-dimethylpiperazino)carbonyl]imidazo[1,5a]quinoline-3-carboxylate.

* * * * *